United States Patent
Penman et al.

(10) Patent No.: US 12,239,347 B2
(45) Date of Patent: Mar. 4, 2025

(54) PATELLA BONE PLATE AND METHODS OF FIXATION

(71) Applicant: DePuy Synthes Products, Inc., Raynham, MA (US)

(72) Inventors: Jessica Penman, West Chester, PA (US); William N. Woodburn, Sr., Mickleton, NJ (US); Eladio Saura-Sanchez, Elche (ES); Daniel Andermatt, Zuchwil (CH); Arabella Fontana, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/301,476

(22) Filed: Apr. 17, 2023

(65) Prior Publication Data

US 2023/0248405 A1    Aug. 10, 2023

Related U.S. Application Data

(63) Continuation of application No. 17/819,560, filed on Aug. 12, 2022, now Pat. No. 11,660,132, which is a continuation of application No. 16/943,218, filed on Jul. 30, 2020, now Pat. No. 11,413,078, which is a continuation of application No. 16/127,678, filed on Sep. 11, 2018, now Pat. No. 10,765,462.

(51) Int. Cl.
*A61B 17/80* (2006.01)

(52) U.S. Cl.
CPC ...... *A61B 17/8061* (2013.01); *A61B 17/8052* (2013.01); *A61B 17/8085* (2013.01); *A61B 17/8057* (2013.01)

(58) Field of Classification Search
CPC . A61B 17/80; A61B 17/8052; A61B 17/8057; A61B 17/8061; A61B 17/8085
See application file for complete search history.

(56) References Cited

U.S. PATENT DOCUMENTS

| | | |
|---|---|---|
| 4,240,162 A | 12/1980 | Devas |
| 5,139,497 A | 8/1992 | Tilghman et al. |
| 5,201,737 A | 4/1993 | Leibinger et al. |
| 5,578,036 A | 11/1996 | Stone et al. |

(Continued)

FOREIGN PATENT DOCUMENTS

| | | |
|---|---|---|
| CN | 202211744 U | 5/2012 |
| CN | 202446238 U | 9/2012 |

(Continued)

OTHER PUBLICATIONS

Arthrex, Stephan Winkler Illustrations, Anatomically Research/Medical, 2015, 7 pages.

(Continued)

*Primary Examiner* — Larry E Waggle, Jr.
(74) *Attorney, Agent, or Firm* — BakerHostetler

(57) ABSTRACT

A patella fracture fixation system includes a bone plate that is configured to be implanted along an anterior approach. The bone plate has a fixation hub and a plurality of fixation nodes that are connected to the fixation hub. The fixation hub and the fixation nodes can define respective fixation holes. The bone plate can further include legs that are configured to be bent around respective inferior aspects of the patella.

13 Claims, 15 Drawing Sheets

(56) References Cited

U.S. PATENT DOCUMENTS

| | | |
|---|---|---|
| 5,593,450 A | 1/1997 | Scott et al. |
| 5,690,631 A | 11/1997 | Duncan et al. |
| 5,718,705 A | 2/1998 | Sammarco |
| 5,743,913 A | 4/1998 | Wellisz |
| 5,785,712 A | 7/1998 | Runciman et al. |
| 5,814,048 A | 9/1998 | Morgan |
| 5,961,519 A | 10/1999 | Bruce et al. |
| 6,093,188 A | 7/2000 | Murray |
| 6,093,201 A | 7/2000 | Cooper et al. |
| 6,206,881 B1 * | 3/2001 | Frigg ............... A61L 31/06 606/76 |
| 6,221,075 B1 | 4/2001 | Toermala et al. |
| RE37,249 E | 6/2001 | Leibinger et al. |
| 6,348,052 B1 | 2/2002 | Sammarco |
| 6,652,530 B2 | 11/2003 | Ip et al. |
| 6,929,646 B2 | 8/2005 | Gambale |
| 6,960,211 B1 | 11/2005 | Pfefferle et al. |
| 7,220,263 B2 | 5/2007 | Cordaro |
| 7,335,204 B2 | 2/2008 | Tornier |
| 7,500,976 B2 | 3/2009 | Suh |
| 7,740,634 B2 | 6/2010 | Orbay et al. |
| D623,743 S | 9/2010 | Den et al. |
| 7,963,979 B2 | 6/2011 | Phillips et al. |
| 8,147,493 B2 | 4/2012 | Dutoit et al. |
| 8,246,663 B2 | 8/2012 | Lovald et al. |
| 8,257,403 B2 | 9/2012 | Den et al. |
| 8,261,750 B1 | 9/2012 | Barry |
| 8,298,292 B2 | 10/2012 | Swords et al. |
| 8,343,196 B2 | 1/2013 | Schneider |
| 8,372,123 B2 | 2/2013 | Smisson et al. |
| 8,512,384 B2 | 8/2013 | Beutter et al. |
| 8,551,143 B2 | 10/2013 | Norris et al. |
| 8,728,126 B2 | 5/2014 | Steffen |
| 8,808,334 B2 | 8/2014 | Strnad et al. |
| 8,906,071 B2 | 12/2014 | Norris et al. |
| 8,906,072 B2 | 12/2014 | Norris et al. |
| 8,906,073 B2 | 12/2014 | Norris et al. |
| 9,387,022 B2 * | 7/2016 | Koay ............... A61B 17/866 |
| 9,517,097 B2 | 12/2016 | Rise et al. |
| 10,004,603 B2 | 6/2018 | Appenzeller et al. |
| 10,327,824 B2 | 6/2019 | Ricker et al. |
| 10,765,462 B2 | 9/2020 | Penman et al. |
| 11,039,868 B2 | 6/2021 | Ricker et al. |
| 11,690,658 B2 | 7/2023 | Helfet et al. |
| 2004/0039395 A1 | 2/2004 | Coon et al. |
| 2004/0102775 A1 | 5/2004 | Huebner |
| 2005/0261780 A1 | 11/2005 | Heino et al. |
| 2006/0025772 A1 | 2/2006 | Leibel et al. |
| 2008/0009872 A1 | 1/2008 | Vaughen et al. |
| 2008/0119895 A1 | 5/2008 | Manceau |
| 2009/0182383 A1 | 7/2009 | Prybyla et al. |
| 2009/0204121 A1 | 8/2009 | Cavallazzi et al. |
| 2013/0090694 A1 | 4/2013 | Norris et al. |
| 2014/0058510 A1 | 2/2014 | Appenzeller et al. |
| 2014/0316472 A1 | 10/2014 | Rise et al. |
| 2017/0065315 A1 | 3/2017 | Helfet et al. |
| 2017/0105775 A1 * | 4/2017 | Ricker ............... A61B 17/1767 |
| 2019/0000516 A1 | 1/2019 | Vickaryous |

FOREIGN PATENT DOCUMENTS

| | | |
|---|---|---|
| CN | 203074840 U * | 7/2013 |
| CN | 203244448 U | 10/2013 |
| CN | 203935262 U | 11/2014 |
| CN | 204092147 U | 1/2015 |
| CN | 108366803 A | 8/2018 |
| EP | 0520177 A1 | 12/1992 |
| EP | 0820730 B1 | 1/2002 |
| EP | 2030596 A1 | 3/2009 |
| EP | 2923676 A1 | 9/2015 |
| FR | 2706278 A1 | 12/1994 |
| GB | 2437492 A | 10/2007 |
| GB | 2471648 A | 1/2011 |
| WO | 2013/055858 A1 | 4/2013 |
| WO | 2017/066682 A1 | 4/2017 |

OTHER PUBLICATIONS

Carpenter JE, Kasman RA, Patel N, Lee ML, Goldstein SA Biomechanical evaluation of current patella fracture fixation techniques. J Orthop Trauma. 1997;11(5):351-356.

DePuy Synthes, Variable Angle LCP Mesh Plate 2.4/2.7. Part of the Variable Angle LCP Forefoot/Midfoot System 2.4/2.7., Surgical Technique, Sep. 2015, 32 pages.

Gosal HS, Singh P, Field RE. Clinical experience of patellar fracture fixation using metal wire or non-absorbable polyester—a study of 37 cases. Injury. 2001;32(2):129-135.

Konigsee Implantate, Variabel winkelstabile Patella-Platte, Variable angle-stable Patella-plate, titan/Titanium, Aug. 2013, 16 pages (with translation).

Matejcic A, Puljiz Z, Elabjer E, Bekavac-Beslin M, Ledinsky M. Multifragment fracture of the patellar apex: Basket plate osteosynthesis compared with partial patellectomy. Arch Orthop Trauma Surg. 2008;128(4):403-408.

Matejcic A, Smiljanic B, Bekavac-Beslin M, Ledinsky M, Puljiz Z. The basket plate in the osteosynthesis of comminuted fractures of distal pole of the patella. Injury, 2006;37(6):525-530.

Medartis, Orbital Plating System OPS 1.5, MODUS Midface, Surgical Technique, Jun. 2013, 12 pages.

Orthopedic Implant—Orthopedic Implants Exporter from Ahmedabad, Maxillofacial Implants plates, https://www.indiamart.com/uteshiyamedicare/orthopedic-implant.html, Aug. 3, 2017, 2 pages.

Taylor BC, Mehta S, Castaneda J, French BG, Blanchard C. Plating of patella fractures: Techniques and outcomes. J Orthop Trauma. 2014;28(9):e231-5.

Thelen S, Betsch M, Schneppendahl J, et al. Fixation of multifragmentary patella fractures using a bilateral fixed-angle plate. Orthopedics. 2013;36(11):e1437-43.

Thelen S, Schneppendahl J, Baumgartner R, et al. Cyclic long-term loading of a bilateral fixed-angle plate in comparison with tension band wiring with K-wires or cannulated screws in transverse patella fractures. Knee Surg Sports Traumatol Arthrosc. 2013;21(2):311-317.

Thelen S, Schneppendahl J, Jo pen E, et al. Biomechanical cadaver testing of a fixed-angle plate in comparison to tension wiring and screw fixation in transverse patella fractures. Injury. 2012;43(8):1290-1295.

Tian et al., Cannulated Screw and Cable are Superior to Modified Tension Band in the Treatment of Transverse Patella Fractures, Ciin. Orthop. Relat. Res, 2011, 469:3429-3435.

Vajapey et al., Contourable craniofacial mesh plate osteosynthesis of patellar fractures: A new, low-profile fixation technique, Journal of Clinical Orthopaedics and Trauma, 2019, 6 pages.

Wendl et al., Frakturen der Kniescheibe, Trauma und Berufskrankheit, vol. 4, issue 1, Apr. 2002, 30-37 (with English abstract).

Wild et al., Fixed-Angle Plates in Patella Fractures—A Pilot Cadaver Study, European Journal of Medical Research, Jan. 2011 16: 41-46.

Wild M, Eichler C, Thelen S, Jungbluth P, Windolf J, Hakimi M. Fixed-angle plate osteosynthesis of the patella—an alternative to tension wiring? Clin Biomech (Bristol, Avon). 2010;25(4):341-347.

* cited by examiner

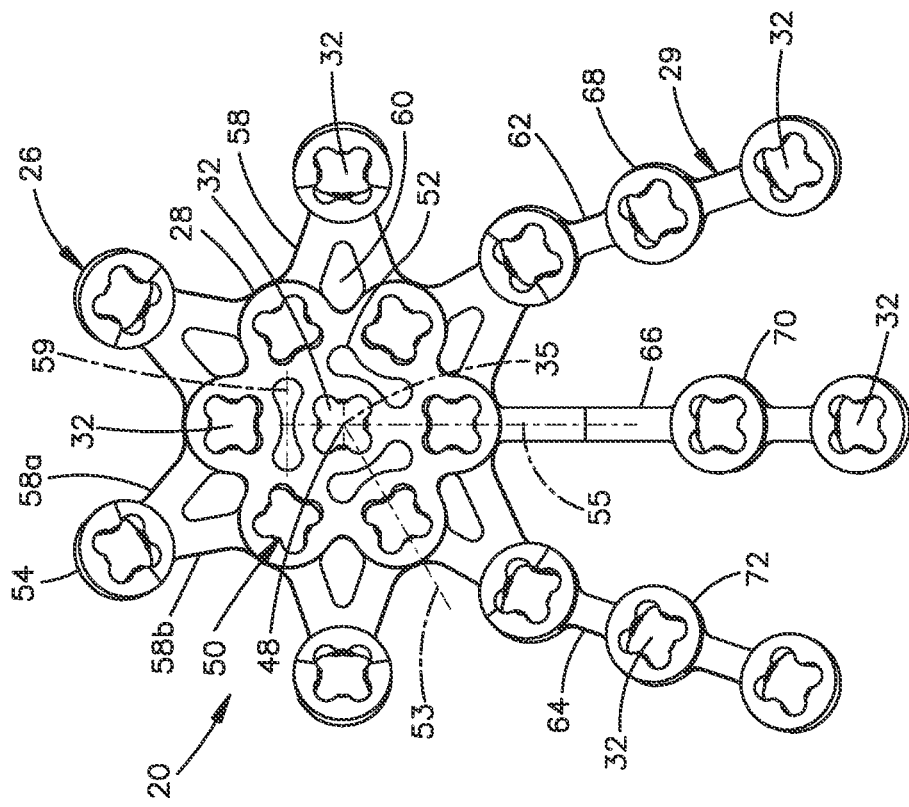
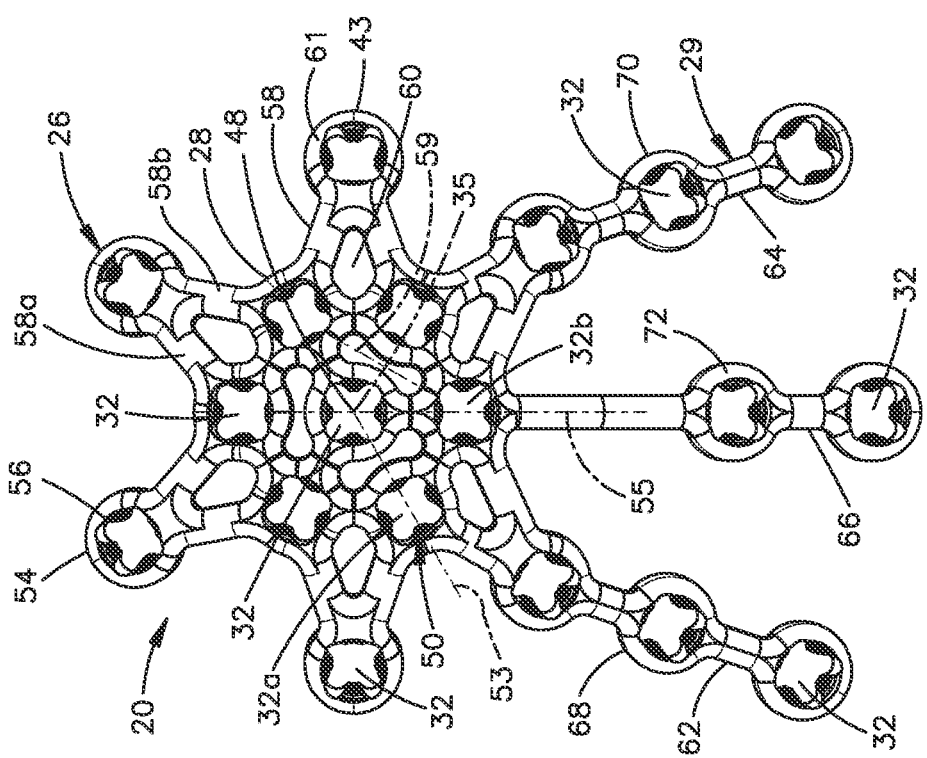

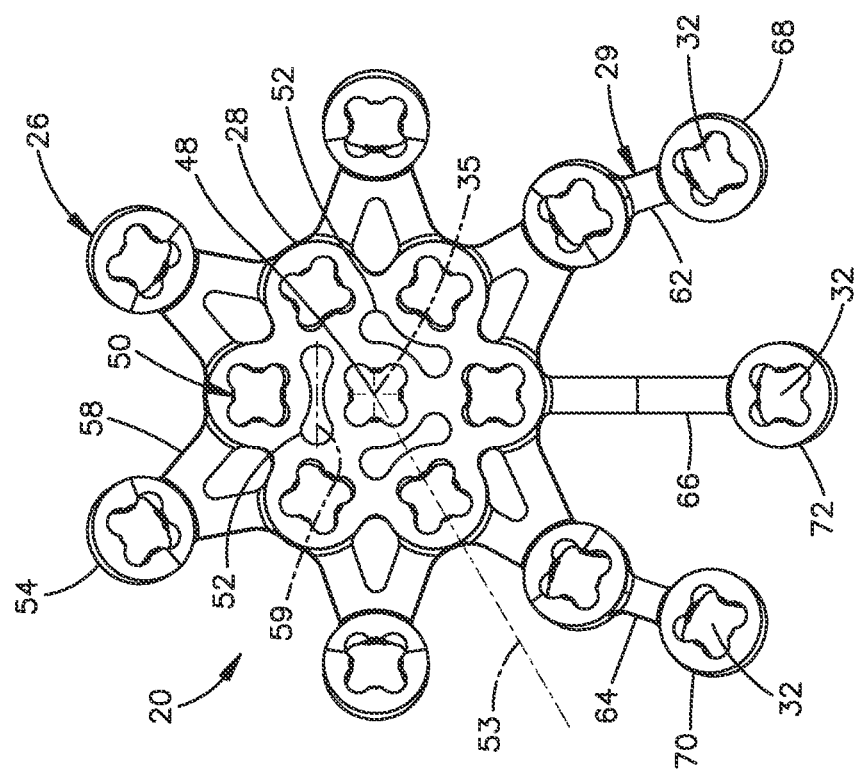

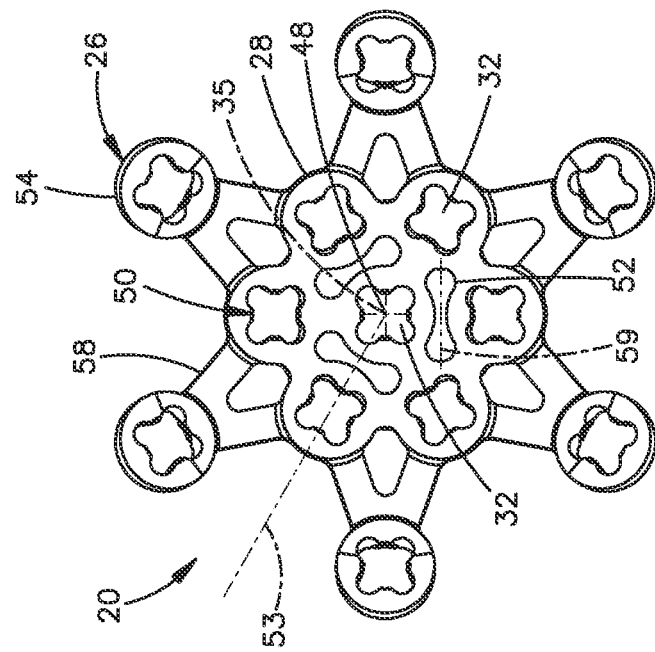
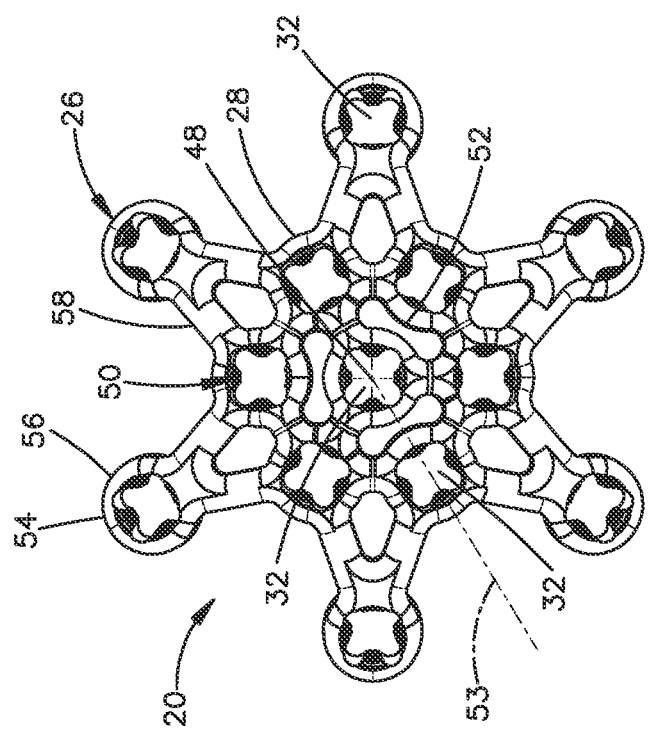

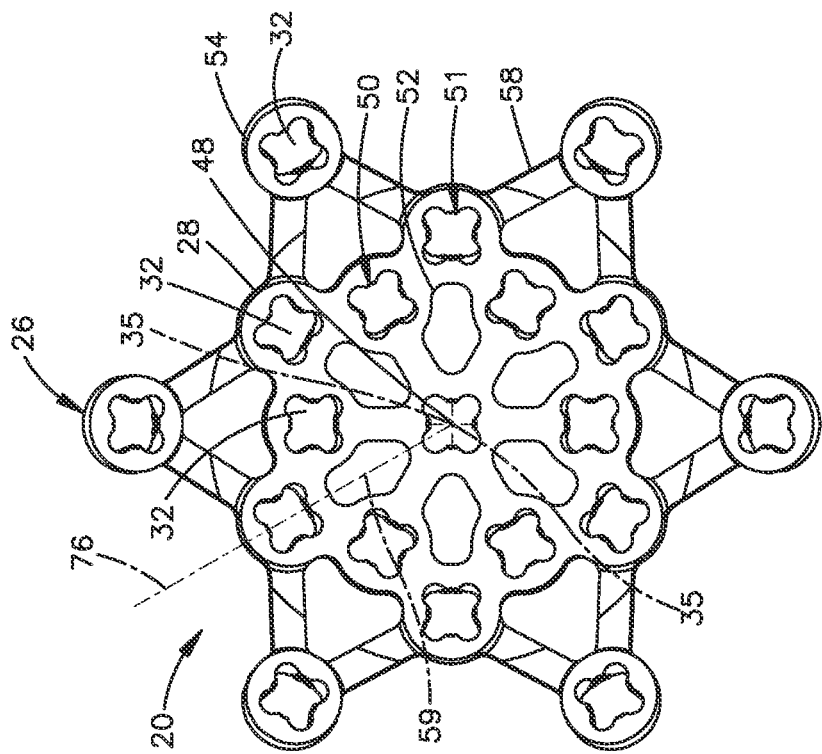
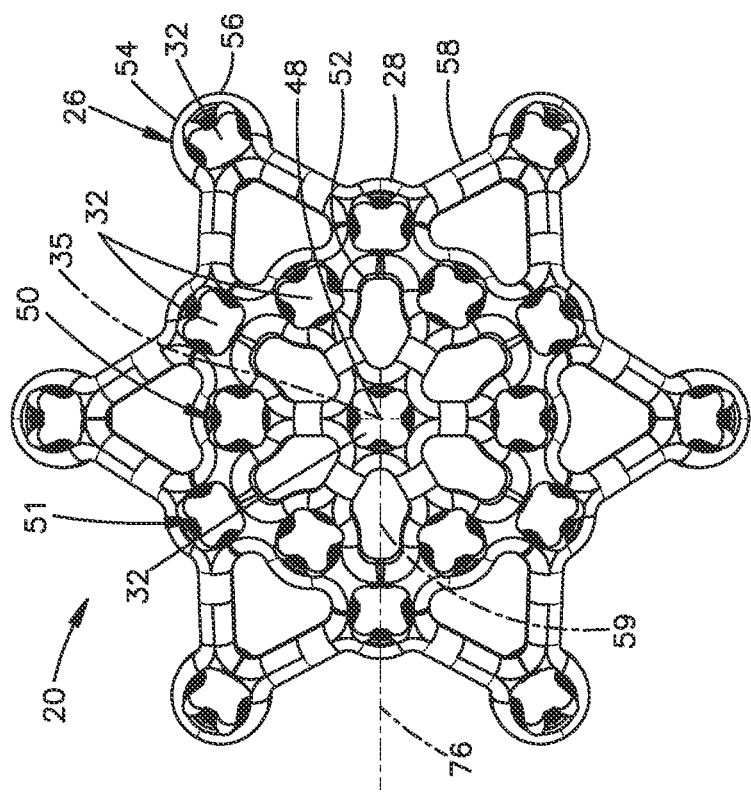

PATELLA BONE PLATE AND METHODS OF FIXATION

CROSS-REFERENCE TO RELATED APPLICATIONS

This is a continuation of U.S. patent application Ser. No. 17/819,560 filed Aug. 12, 2022, which is a continuation of U.S. patent application Ser. No. 16/943,218 filed Jul. 30, 2020, now U.S. Pat. No. 11,413,078, which is a continuation of U.S. patent application Ser. No. 16/127,678 filed Sep. 11, 2018, now U.S. Pat. No. 10,765,462, the disclosures of each of which are hereby incorporated by reference as if set forth in their entireties herein.

BACKGROUND

Patella fractures represent approximately 1% of all fractures and can be debilitating injuries resulting in extensor mechanism weakness, decreased knee range of motion, anterior knee pain, and degenerative patellofemoral arthritis. The limited soft tissue coverage and importance of the patella in knee extensor mechanism function has made operative treatment of these injuries challenging.

Historically, patellar fractures were treated non-operatively, which was thought to allow for adequate pain relief and partial restoration of extensor mechanism function. However, as surgical knowledge and technique has advanced, management of these injuries has evolved from non-operative care or patellectomy to anatomic reduction and internal fixation with a goal of osseous union.

Today, a non-operative treatment course can be recommended for non-displaced fractures of the patella, particularly when the fracture is non-displaced, the articular surface is not disrupted, and the extensor mechanism is intact. However, a disruption of the articular surface of as little as 2 mm or separation of bone fragments by as little as 3 mm is conventionally associated with an unacceptable risk of unsuitable bone healing. Additionally, patients with patella fractures often have concurrent retinacular tears that can result in fracture displacement and disruption of the extensor mechanism. Further, because of the important role of the patella in maintaining normal kinematics of the knee, operative management is considered to be the treatment of choice for patella fractures when patellar bone fragments are displaced, or the articular surface is disrupted.

One construct commonly used for the operative fixation of patella fractures is a tension band. In particular, an anterior tension band is applied by passing wires or braided cables or sutures behind previously implanted K-wires at the superior and inferior poles, crossing them, and twisting the ends to create a figure-eight pattern. Further, a wire or braided cable can be wrapped circumferentially around the patella directly on bone at a location anterior to the previously placed wires, and is tightened by twisting. A modification of this technique can be performed by replacing the K-wires with cannulated screws, such that a wire or braided cable or suture can be passed through the cannulated screws to create the anterior tension band with a figure-eight configuration, followed by application of a cerclage wire directly on the circumference of the patella.

While tension band constructs are the most common method of fixation, anterior knee pain, failure of the construct, and functional limitation with tension band fixation have all been reported. Further, this technique often fails to address inferior pole comminution commonly seen in fractures of the patella.

More recently, biomechanical studies have shown an advantage to fixation of patella fractures with plating constructs as opposed to tension band fixation. While various different patella plating constructs in use today can achieve satisfactory fracture reductions, the ultimate outcomes are often ineffective and clinically poor. In particular, despite reliable fracture healing and restoration of the extensor mechanisms, outcomes often remain unacceptable with convention techniques. A common misconception among surgeons is that patients recovering from patella fracture fixation mostly do well. However, this is likely because patients are not followed long enough post-operatively. Anterior knee pain after patellar fracture fixation is a common complaint during daily activity. Potential causes include patella baja, extensor mechanism malalignment, articular injury and posttraumatic arthritis, painful implants, or avascular necrosis. This anterior knee pain leads to limited rehabilitation and functional impairment.

Still another surgical option is to perform a partial or total patellectomy, though these procedures are typically reserved for extreme cases such as open injuries. Patellectomy procedures produce a high risk for creating patella baja, and bone-to-bone healing is preferred over tendon-to-bone healing. Also, a partial patellectomy procedure is likely to disrupt the main blood supply to the patella as it enters the inferior pole.

In other instances of an isolated inferior pole fracture that does not include the articular surface, fracture repairs are sometimes performed with what are commonly known as Krackow sutures. In particular, Krackow sutures are placed on the medial and lateral aspects of the patellar tendon, and retrograde drill holes are created from the interior pole to the superior apex of the patella. The sutures are then passed through the drill holes and tied over the superior bony edge of the patella.

SUMMARY

In one aspect of the present disclosure, a patella bone plate includes a fixation body that, in turn, includes a fixation hub and a plurality of fixation nodes. The fixation hub can have an inner surface configured to face the patella bone and an outer surface opposite the inner surface. The fixation hub can define include an array of fixation holes that extend from the inner surface to the outer surface. The fixation nodes can extend from the fixation hub and can each define a respective fixation hole. The bone plate can further include at least one leg that extends out from the body, the at least one leg being deformable and having a length sufficient so as to wrap around an inferior rim of the patella, the at least one leg including at least one fixation hole.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings:

FIG. 3A is a top plan view of the bone plate illustrated in FIG. 1A, shown having a fixation body and fixation legs extending from the fixation body;

FIG. 3B is a bottom plan view of the bone plate illustrated in FIG. 3A;

FIG. 4A is a top plan view of a bone plate similar to the bone plate illustrated in FIG. 3A, but shown having shorter fixation legs;

FIG. 4B is a bottom plan view of the bone plate illustrated in FIG. 4A.

FIG. 5A is a top plan view of a bone plate similar to the bone plate illustrated in FIG. 3A, but shown without fixation legs in one example.

FIG. 5B is a bottom plan view of the bone plate illustrated in FIG. 5A;

FIG. 8A is a top plan view of a bone plate similar to the bone plate illustrated in FIG. 6A, but shown without fixation legs;

FIG. 8B is a bottom plan view of the bone plate illustrated in FIG. 8A;

DETAILED DESCRIPTION

Figure 1A:
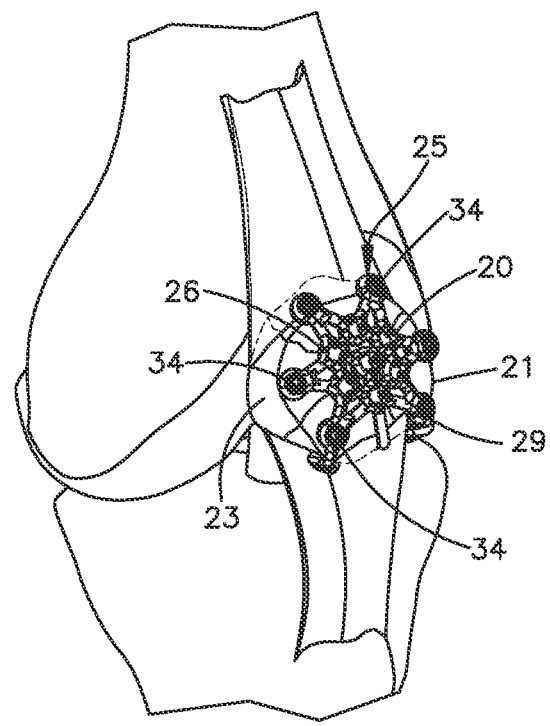
FIG. 1A is a perspective view of a patella fixation system including a bone plate and a plurality of bone anchors secured to a fractured patella through fixation holes of the bone plate.
Figure 1B:
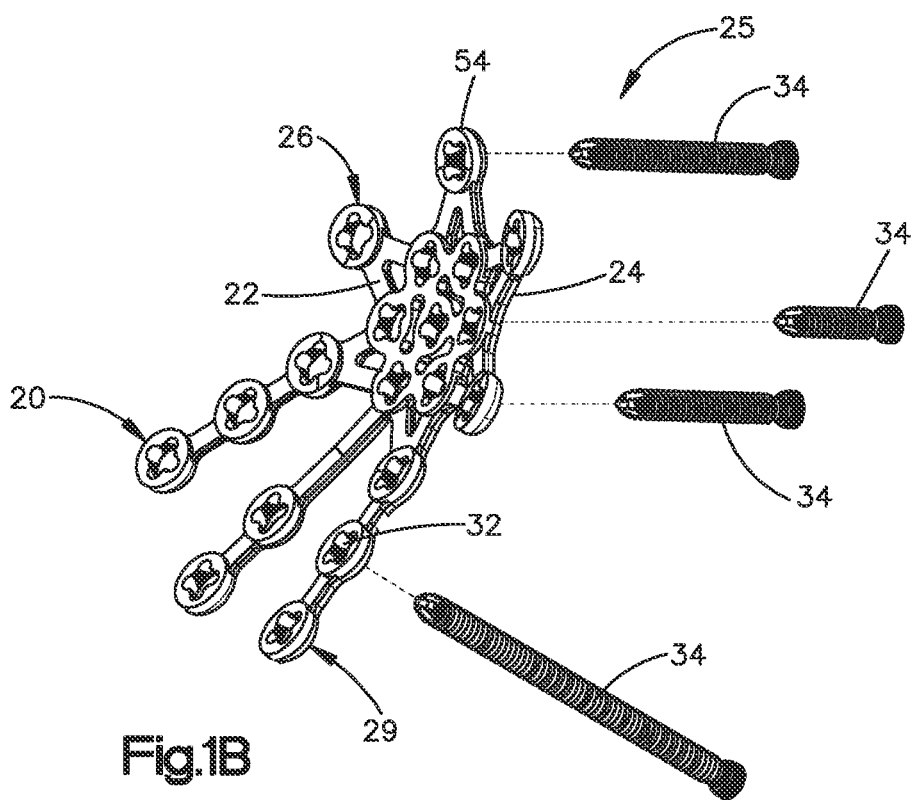
FIG. 1B is an exploded perspective view of the patella fixation system illustrated in FIG. 1A.

Referring initially to FIGS. 1A-1B, bone plate 20 is configured for fixation to an underlying bone 21. The underlying bone 21 can be defined by the patella bone 23. In particular, the bone plate 20 can be configured to be fixed to a fractured patella bone so as to stabilize the fractured patella so as to promote healing. As will be appreciated from the description below, the bone plate 20 can be configured to stabilize a heavily comminuted fractures of the patella bone. The bone plate 20 can be a titanium bone plate, a stainless steel bone plate, or any alternative suitable biocompatible made as desired that possesses the requisite strength for patella fixation.

The bone plate 20 can define an inner surface 22 that is designed and configured to face the underlying bone 21, and an outer surface 24 opposite the inner surface 22. At least a portion of the inner surface 22 can further be configured to abut the underlying bone 21. The bone plate 20 can include a fixation body 26 that includes a fixation hub 28 that is configured to secure to an anterior aspect of the patella 23. The fixation body 26 can further include at least one fixation node 54 such as a plurality of fixation nodes 54 that are disposed radially outward with respect to the fixation hub 28. The inner surface 22 at the fixation body 26 can be concave. Thus, the inner surface 22 at either or both of the fixation hub 28 and the fixation nodes 54 can be concave. In one example, the inner surface 22 at the fixation body 26 can be substantially dome shaped. The term "substantially" as used herein with respect to sizes and shapes can include any value within 20% of the stated size and shape unless otherwise indicated. In some examples, the bone plate 20 can further include at least one fixation leg 29 that extends out from the fixation body 26. As will be appreciated from the discussion below, the fixation legs 29 extend inferiorly from the fixation body 26 when the fixation hub is positioned on the anterior surface of the patella 23. A first one of the fixation legs 29 can be configured to be secured to an inferior medial aspect of the patella 23. A second one of the fixation legs 29 can be configured to be secured to an inferior lateral aspect of the patella 23. A third one of the fixation legs 29 can be configured to be secured to an inferior pole of the patella 23. Thus, the fixation legs 29 can include a middle leg and a pair of outer legs disposed on opposed sides of the middle leg.

The hub 28 can define a plurality of fixation holes 32 that extend from the outer surface 24 to the inner surface 22. The fixation holes 32 are configured to receive a bone anchor 34 that threadedly purchases with the patella. In this regard, it should be appreciated that the bone anchor 34 can threadedly purchase with the patella bone or with fractured patellar bone fragments depending on the position of the respective fixation hole 32. Further, the bone anchors 34 can have different lengths as desired. Thus, at least one of the bone anchors 34 can be sized to be driven into multiple bone fragments if desired.

A patella fixation system 25 can include the bone plate 20 and at least one bone anchor 34 that is configured to secure the bone plate 20 to the underlying bone. In one example, at least one of the fixation holes 32 up to all of the fixation holes 32 can be configured as a locking hole having at least one thread 36 that is configured to threadedly purchase with the bone anchor 34 when the bone anchor is driven into the fixation hole 32.

In one example, the bone anchors 34 can include an anchor head 38 and a shaft 40 that extends from the anchor head 38 along a central anchor axis 39. The shaft 40 can be threaded along a portion of its length up to an entirety of its length, for instance when the bone anchor 34 is provided as a screw. Thus, rotation of the bone anchor 34 in a first direction while the shaft 40 is purchased in the underlying bone can cause the shaft 40 to drive into the underlying bone 21. Conversely, rotation of the bone anchor 34 in a second direction opposite the first direction while the shaft 40 is purchased in the underlying bone can cause the shaft 40 to be removed from the underlying bone 21. In another example, the shaft 40 can be smooth along its length, for instance when the bone anchor 34 is configured as a nail, rivet, or pin. In one example, the anchor head 38 can be configured as a locking head whereby an external surface of the anchor head 38 is threaded. The anchor head 38 is configured to threadedly purchase with the bone plate 20 in the fixation hole 32. The fixation hole 32 extends along a central hole axis 33 from the outer surface 24 to the inner surface 22.

Figure 2A:
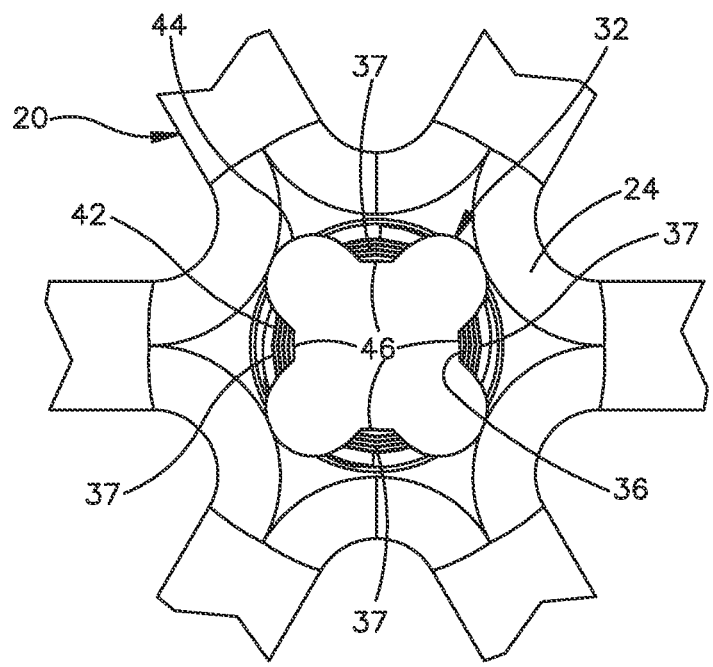
FIG. 2A is an enlarged top plane view of a portion of the bone plate illustrated in FIG. 1A, showing one of the fixation holes.
Figures 2B, 2C:
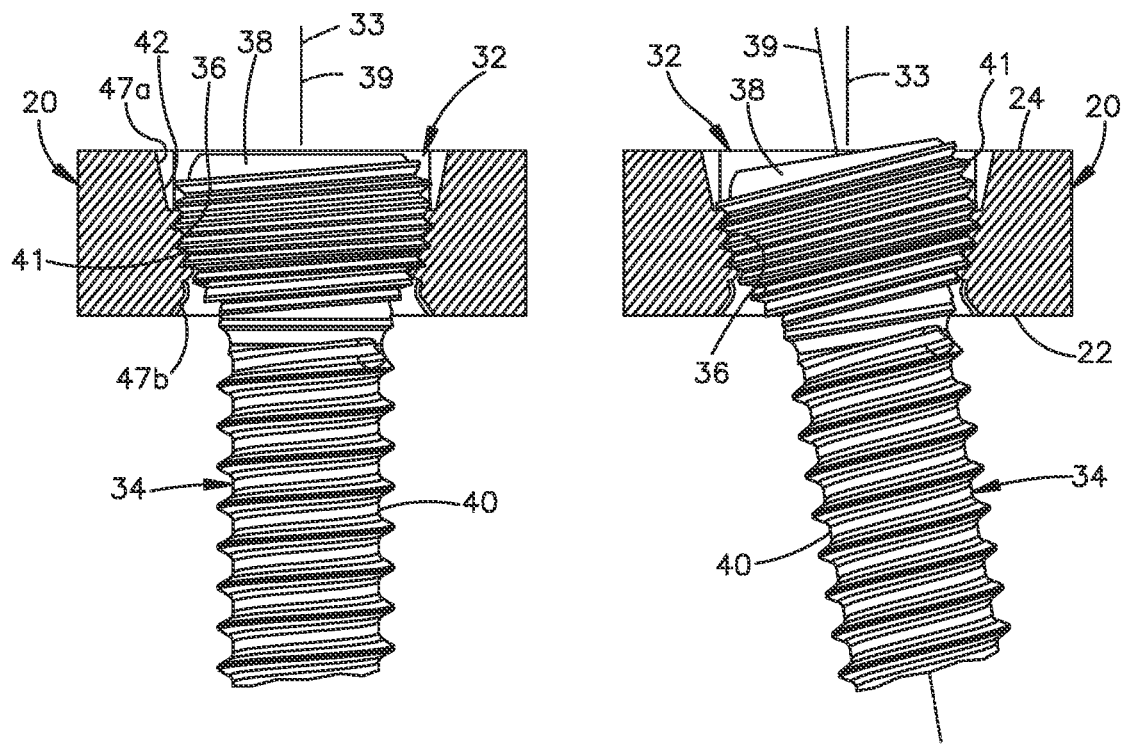
FIG. 2B is a sectional elevation view of the fixation hole illustrated in FIG. 2A with a variable-angle bone screw threadedly purchased therein in a first angular orientation.
FIG. 2C is a sectional elevation view of the fixation hole illustrated in FIG. 2B, showing the variable-angle bone screw threadedly purchased therein in a second angular orientation different than the first angular orientation.
Figure 3D:
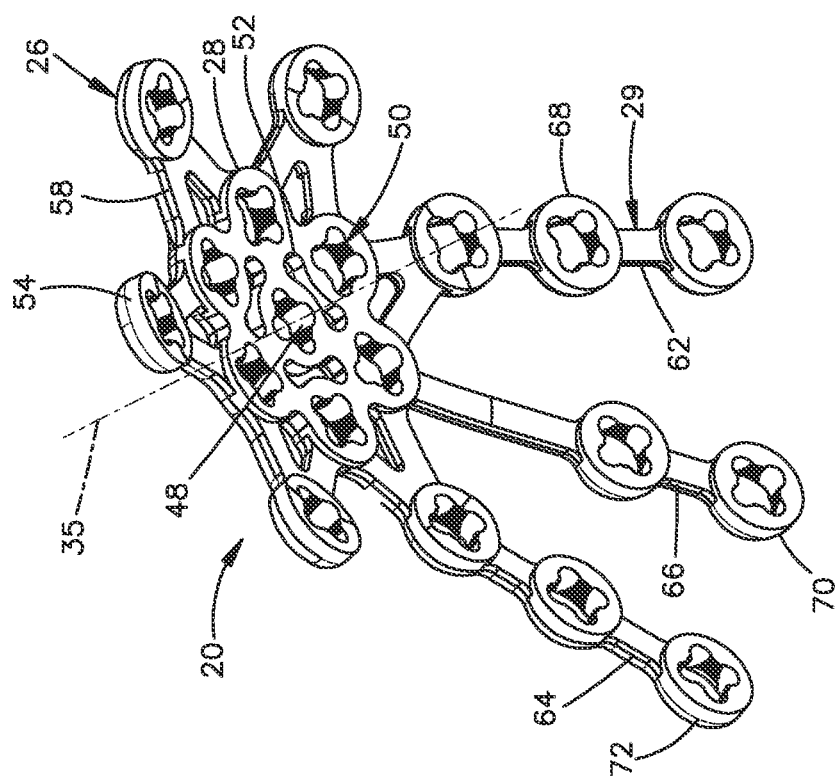
FIG. 3D is a bottom perspective view of the bone plate illustrated in FIG. 3A.
Figure 3C:
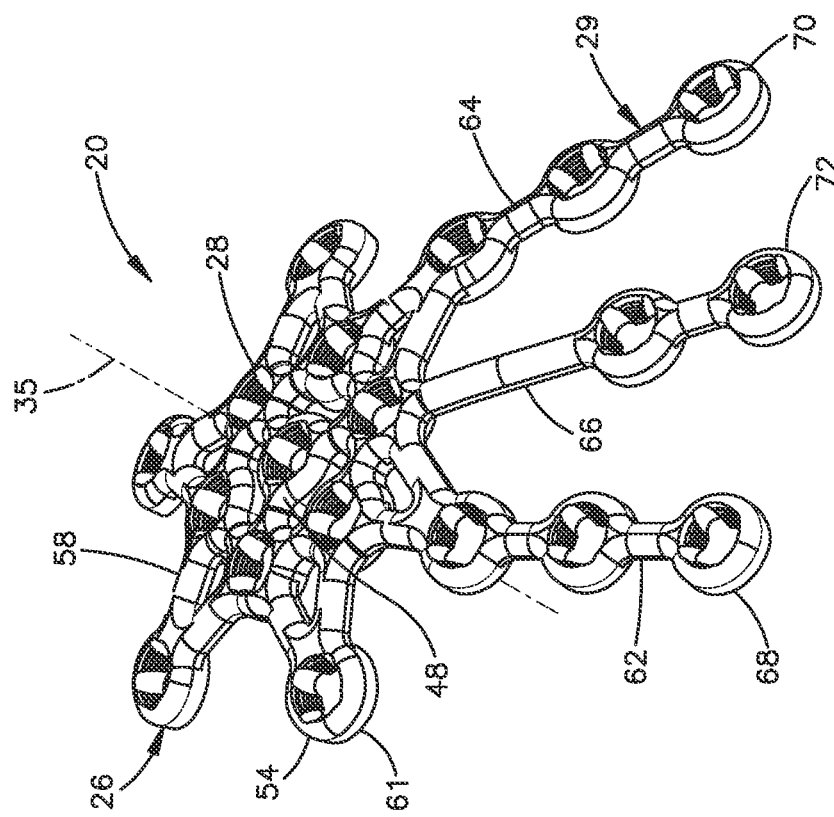
FIG. 3C is a top perspective view of the bone plate illustrated in FIG. 3A.
Figure 3E:
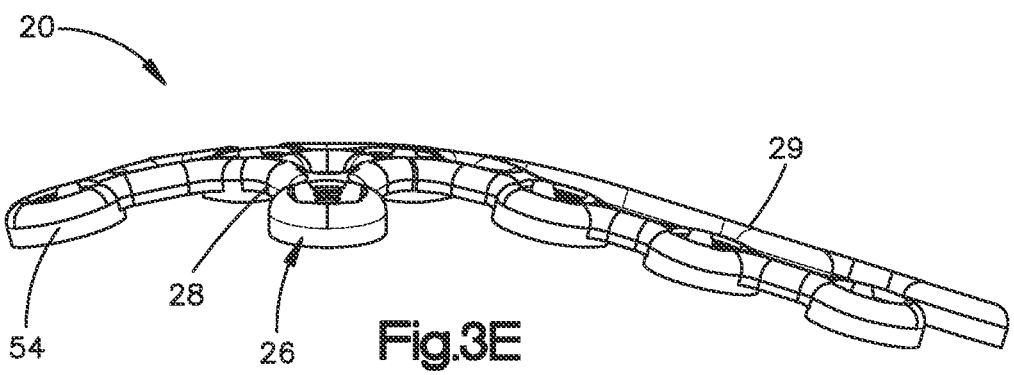
FIG. 3E is a side elevation view of the bone plate illustrated in FIG. 3A.
Figure 3F:
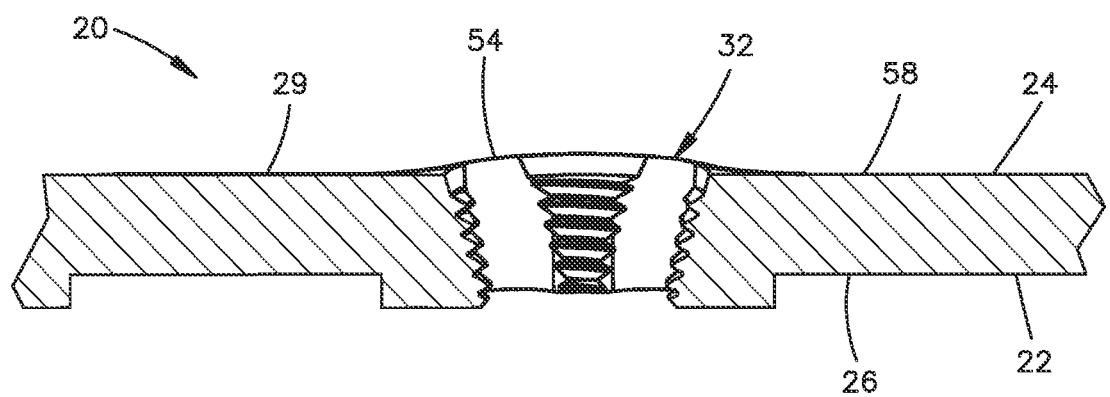
FIG. 3F is a sectional elevation view of a portion of the bone plate illustrated in FIG. 3A.

Referring now also to FIGS. 2A-2C, the fixation hole 32 can be configured as a variable angle fixation hole whereby the anchor head 38 is configured to threadedly purchase with the bone plate 20 in the fixation hole 32 when the central anchor axis 39 and the central hole axis 33 define any angle therebetween within a predetermined range of angles whereby the shaft 40 is driven into the underlying bone 21. Accordingly, the angle defined by the central anchor axis 39 and the central hole axis 33 is adjustable within the range of angles, such that the central anchor axis 39 is angularly offset with respect to the central hole axis 33 at any angle as desired within the range of angles. In one example, the bone anchor 34 can be inserted into the fixation hole 32 such that the central anchor axis 39 is coaxial with the central hole axis 33 or at any angle relative to the central hole axis 33 within the range of angles. The range of angles can be between and include 0 degrees and 15 degrees. The outer surface of the anchor head 38 can be round or substantially spherical as illustrated in FIGS. 3E-F, or substantially conically shaped or alternatively shaped as desired.

In accordance with the illustrated example, the fixation hole 32 can be defined by an interior surface 42 that extends from the outer surface 24 to the inner surface 22. The fixation hole 32 can be configured as a variable-angle locking hole in one example. Thus, the interior surface 42 can include a plurality of scalloped portions 44, which can be unthreaded, that extend into the interior surface and interrupt the at least one thread 36. Accordingly, the scalloped portions 44 separate the at least one thread 36 into a corresponding plurality of columns 46 of thread segments 37 that are spaced from each other, such that ones of the scalloped portions 44 are disposed between adjacent ones of the columns 46 along a circumferential direction about the central hole axis 33. In one example, the fixation hole 32 can include three scalloped portions 44, four scalloped portions 44, or any suitable alternative number of scalloped portions 44 as desired. Each of the scalloped portions 44, the columns 46, and the anchor head 38 can be shaped substantially as described in U.S. Pat. No. 8,343,196, the disclosure of which is hereby incorporated by reference as if set forth herein.

The thread segments 37 can be defined by any number of threads 36 as desired. The threads 36 can be adapted and configured to engage external threads 41 of the anchor head 38 and can extend along paths which, if continued across the gaps defined by the scalloped portions 44, would form a helical threading with a substantially constant pitch corresponding to the external threads 41 of the anchor head 38. The anchor head 38 can have an externally spherical shape that allows the external threads 41 to threadedly purchase with the thread segments 37 whether the bone anchor 34 is inserted co-axially with the central hole axis 33 as shown in FIG. 2B, or angularly offset from the central hole axis 33 within the range of angles, as shown in FIG. 2C.

The columns 46 can have any suitable shape as desired. In accordance with one example, the fixation hole can have a complex shape including a first portion 47a that tapers radially inward toward the central hole axis 33 from the outer surface 24 toward the inner surface 22, and a second portion 47b that tapers radially outward away from the central hole axis 33 from the first portion 47a to the inner surface 22 of the bone plate 20. The first and second portions 47a and 47b can be unthreaded. The first portions 47a can be arranged along a first substantially conical shape centered on the central hole axis 33, and the second portions 47b can be arranged along a second substantially conical shape centered on the central hole axis 33. The scalloped portions 44 between the columns 46 can be, for example, substantially cylindrically shaped and extend radially outward beyond the first and second conical shapes, thereby extending the range of angulation of the bone anchor 34 when the bone anchor 34 is inserted into the fixation hole 32, for instance when the shaft 40 extends into one of the scalloped portions 44.

In accordance with the illustrated embodiment, the fixation hole 32 can include four columns 46 of thread segments 37 that are spaced about the circumference of the fixation hole 32. For instance, columns 46 of thread segments 37 can be spaced substantially equidistantly from one another about the circumference of the fixation hole 32. Thus, the scalloped portions 44 can define widths measured circumferentially about the central hole axis 33 that are substantially equal to one another. It should be appreciated, however, that the fixation hole 32 can include any number of columns 46 arranged in any number of patterns as desired. Furthermore, it should be appreciated that the columns 46 can alternatively be spaced about the circumference of the fixation hole 32 by varying distances, and the columns 46 and scalloped portions 44 can have different circumferential widths as well.

While one or more of the fixation holes 32 up to all of the fixation hole 32 can be configured as a variable angle locking hole in the manner described above, it should be appreciated that one or more of the fixation holes 32 up to all of the fixation holes 32 can be alternatively constructed as desired. For instance, at least one of the fixation holes 32 can be configured as a standard-type fixed angle locking hole. In particular, the bone plate 20 is configured to threadedly mate with the anchor head 38 in the fixation hole 32 only when the bone anchor 34 is oriented at a predetermined orientation with respect to the central hole axis 33. In this example, the thread 36 can extend continuously along its respective helical path along multiple revolutions about the central hole axis 33 so as to purchase with the anchor head 38. The predetermined orientation can be a nominal orientation whereby the central anchor axis 39 is coincident with the central hole axis 33. Alternatively, the predetermined orientation can be defined when the central anchor axis 39 is oriented oblique to the central hole axis 33. In certain examples, the anchor head 38 can be configured to threadedly mate with the bone plate 20 in the fixation hole 32 only when the bone anchor 34 is oriented at the predetermined orientation.

Alternatively or additionally still, at least one of the fixation holes 32 up to all of the fixation holes 32 can be configured as an unthreaded compression hole. Thus, one or more of the bone anchors 34 can be configured as a compression anchor whose anchor head 38 defines a compression head that is configured to bear against the bone plate 20 in the compression hole so as to apply a compressive force against the bone plate 20 toward or against the underlying bone. The interior surface 42 can extend between the outer surface 24 and the inner surface 22 so as to at least partially define the fixation hole 32. During operation, the shaft 40 of the bone anchor 34 can be inserted through the fixation hole 32 and driven into the underlying bone 21. When at least a portion of the shaft 40 is threaded, rotation of the bone anchor 34 causes the anchor head 38 to compress against the interior surface 42. As a result, the anchor head 38 causes the bone plate 20 to apply a compressive force against the underlying bone 21. The external surface of the anchor head 38 can be unthreaded. Similarly, at least a portion up to an entirety of the interior surface 42 that abuts the unthreaded external surface of the anchor head 38 can be unthreaded.

Alternatively or additionally still, at least one other ones of the fixation holes 32 can be a combination hole, whereby a threaded locking hole portion and an unthreaded compression hole portion intersect each other to define the combination hole. The bone anchor 34 can be selectively driven into the threaded locking hole portion and the unthreaded compression hole portion. The threaded locking hole portion can define a variable angle locking hole portion or a standard type locking hole portion as desired.

Referring now to FIGS. 3A-3D, and as described above, the fixation body 26 of the bone plate 20 can include the fixation hub 28 and the at least one fixation node 54 that is disposed radially out with respect to the fixation hub 28. The bone plate 20 can be preformed such that the inner surface 22 at the fixation body 26 can define a concavity. Thus, the outer surface 24 at the fixation body 26 can be convex. In one example, the inner surface at the fixation body 26 can be substantially dome shaped. Thus, the bone plate 20 as-manufactured can generally conform to the patella bone 23. In one example, the dome shape of the inner surface 22 at the fixation body 26 can be defined by any suitable radius as desired. For instance, the radius can in a range from approximately 25 mm to approximately 75 mm. In one example, the range can be from approximately 40 mm to approximately 60 mm. In particular, the radius can be approximately 50 mm. It should be appreciated that the concavity of the inner surface 22 can define any suitable geometry as desired other than a dome. During operation, the inner surface 22 is more preformed to the outer surface of the patella 23 (see FIG. 1A) than conventional flat bone plates. It is envisioned that in some circumstances the fixation body 26 may be manipulated in situ to better confirm to the patella 23. In this regard, it should be appreciated that the fixation body 26 can be flexible and deformable so as to conform the fixation plate 20 to the underlying bone 21.

Referring now to FIGS. 3A-3B, the fixation hub 28 is configured to be secured to one or more bone fragments of the patella 23 as desired. The fixation hub 28 can define a geometric center 48 that defines a central hub axis 35. The fixation hub 28 can define a fixation hole 32 at the geometric center 48. The central hole axis 33 of the fixation hole 32 at the geometric center 48 can be coincident with the central hub axis 35. Thus, reference to the central hole axis 33 of the fixation hole at the geometric center 48 can apply more generally to the central hub axis 35 whether or not the geometric center defines a fixation hole 32.

The fixation hub 28 can further include an array 50 of fixation holes 32. The array 50 can be a circumferential array. The fixation holes 32 of the array 50 can be arranged along a path that extends about the geometric center 48. For instance, the path can be a closed path that surrounds the geometric center 48. In one example, the path of the array 50 can define a circle. The central hub axis 35 can define the center of the circle. The central hole axes 33 (see FIG. 2B) can lie on the circle. In one example, the fixation holes 32 can be spaced equidistantly from each other along the circle. Alternatively, the fixation holes 32 can be spaced at variable distances from each other. Further, while the fixation holes 32 of the array 50 can be arranged on the circular path, it should be appreciated that the fixation holes 32 of the array 50 can be alternatively arranged as desired. For instance, the fixation holes 32 of the array 50 can lie on any curved path. The curved path can define an ellipse in one example. Alternatively, the path can define a polygon. For instance, the central hole axes 33 can define the vertices, respectively, of the polygon. In one example, as illustrated in FIGS. 3A-3B, the polygon can be a regular polygon. Alternatively, the polygon can be an irregular polygon. In this regard, it should be appreciated that the fixation body 26 can be symmetrical or asymmetrical as desired.

In one example, the array 50 can include six fixation holes 32. Thus, the regular polygon can be configured as a hexagon. It should be appreciated, however, that the array 50 can include any number of fixation holes 32 as desired. In one example, the fixation hole 32 at the geometric center 48 and the fixation holes 32 of the array 50 can constitute all fixation holes 32 of the fixation hub 28. Alternatively, the fixation hub 28 can include at least one additional fixation hole 32 in addition to the fixation hole 32 at the geometric center 48 and the fixation holes 32 of the array 50. The at least one additional fixation hole 32 can be disposed between the geometric center 48 and the array 50. Alternatively or additionally, the at least one additional fixation hole 32 can be disposed radially outward of the array 50. Thus, the array 50 can be disposed between the at least one additional fixation hole 32 and the geometric center 48.

The fixation body 26 can include at least one aperture 52 that extends through the fixation hub 28 from the outer surface 24 to the inner surface 22. For instance, the fixation body 26 can include a plurality of apertures 52 that extend through the fixation hub 28 from the outer surface 24 to the inner surface 22. The fixation body 26 can include any number of apertures 52 as desired. Further, the apertures 52 can be of any suitable size and shape as desired. Further still, the apertures 52 can be positioned at any location as desired. In one example, the apertures 52 can be elongate. For instance, the apertures 52 can be elongate along a respective central axis 59. The central axes 59 of the apertures 52 can define tangents along a respective common circle that surrounds the geometric center 48 of the fixation hub 28. Further, the geometric center of the apertures 52 can lie on the respective circle. Thus, the geometric centers of the apertures 52 can be circumferentially aligned with each other. For instance the geometric center 48 of the fixation hub 28 can define the center of the respective circle. Thus, the respective circle of the apertures 52 can be concentric with the circle defined by the path of the array 50 of fixation holes 32. The respective circle of the apertures 52 can define an inner circle of the fixation hub 28. The circle of the array 50 of fixation holes 32 can define an outer circle of the fixation hub 28 that surrounds the inner circle of the fixation hub 28.

The geometric centers of the apertures 52 can be radially aligned with each of the fixation hole 32 at the geometric center 48 and an aligned one 32a of the fixation holes 32 of the array 50, with respect to a top plan view of the bone plate. For instance, the geometric centers of the apertures 52 can lie on a respective straight line 53 that extends from the central hole axis 33 of the fixation hole 32 at the geometric center 48 of the hub 28 to the central hole axis 33 of respective aligned ones of the fixation holes 32 of the array 50. The geometric centers of the apertures 52 can lie on the respective central axes 59. Thus, the respective straight line 53 can be said to intersect the central axis 59 of the apertures. The apertures 52 can be partially defined by respective inner sides that can partially define the fixation hole 32 at the geometric center 48. The apertures 52 can be partially defined by respective outer sides that can partially define the respective aligned ones of the fixation holes 32 of the array 50. The apertures 52 can define respective ends that each lie on respective straight lines 55 that extend from the central hub axis 35 to a location circumferentially between adjacent ones of the fixation holes 32 of the array 50, with respect to one or both of a top plan view and bottom plan view of the bone plate 20. One of the adjacent ones of the fixation holes 32 can be defined by the respective aligned one 32a of the fixation holes 32. The central hole axis 33 of the other 32b of the adjacent ones of the fixation holes 32 can lie on the respective straight line 55 that extends to the central hole axis 33 of the fixation hole 32 at the geometric center 48 of the hub 28 without passing through any of the apertures 52.

As described above, the apertures 52 can be elongate along the respective central axis 59. For instance, the apertures 52 can be dog bone shaped in one example. However, the apertures 52 can define any suitable alternative shape as desired. For instance, the apertures 52 can be oval shaped or rectangular. Alternatively, the apertures 52 can be constructed as a circle, a regular polygon, or an irregular polygon. Further, the apertures 52 can be circumferentially equidistantly spaced from each other. Alternatively, the apertures 52 can be variably spaced from each other. Further still, the apertures 52 can be constructed such that their respective geometric centers are not in circumferential alignment with each other.

The apertures 52 can be sized greater than the fixation holes 32. For instance, the apertures 52 can be sufficiently sized so as to define visualization windows that allow for visibility of the underlying patella. For instance, the user can visualize the patella through the visualization windows both as the bone plate 20 is being placed onto the patella, and after the bone plate 20 has been placed onto the patella. Thus, the surgeon can visually align the fixation holes 32 with respective bone fragments to which the bone plate 20 is to be secured. The apertures 52 can further assist in the malleability of the bone plate 20, which allows the bone plate 20 to be bent as desired so as to better conform to the patella. Further, the apertures 52 can define herniation holes that allow for soft tissue to herniate through the apertures 52.

For instance, when the bone plate 20 is placed against the patella and secured to the patella, soft tissue residing between the patella bone and the bone plate 20 can herniate through the apertures 52, thereby reducing the profile of the bone plate 20 with respect to the epidermis.

With continuing reference to FIGS. 3A-3D, and as described above, the fixation body 26 can include a plurality of fixation nodes 54 that are disposed radially outward with respect to the fixation hub 28. The fixation nodes 54 can be supported by the fixation hub 28. Each of the fixation nodes 54 can define at least one fixation hole 32. Thus, the fixation nodes 54 can be configured to secure to one or more bone fragments of the patella 23 as desired. For instance, each of the fixation nodes 54 can define a single fixation hole 32. In one example, each of the fixation nodes 54 can define an eyelet 56 that, in turn, defines the fixation hole 32. The eyelet 56 can define an annular wall having an inner surface that defines the interior surface 42 of the respective fixation hole 32. The eyelet 56 can further define an outer surface 61 opposite the inner surface that defines an exterior surface 43 of the fixation node 54.

The bone plate 20, and in particular the body 26 of the bone plate 20, can define at least one arm 58, such as a plurality of arms 58, that extends radially outward from the fixation hub 28 to a respective at least one of the fixation nodes 54. Thus, each of the fixation nodes 54 can be attached to the fixation hub 28 by the respective arms 58. For instance, the at least one arm 58 can extend to the outer surface 61 of the eyelet 56. In one example, the at least one arm 58 can include at least one pair of arms 58 that includes first and second arms 58a and 58b. Thus, each of the fixation nodes 54 can be secured to the fixation hub 28 by a respective pair of arms 58. Each pair of arms 58 can be defined by a first arm 58a and a second arm 58b. The arms 58a and 58b of each pair can converge toward each other as they extend from the fixation hub 28 to the respective one of the fixation nodes 54. Each of the arms 58 can be devoid of fixation holes that are designed and configured to receive a fixation screw so as to attach the bone plate 20 to the underlying bone 21. Further, each of the arms 58 can extend from the fixation hub 28 to the respective one of the nodes 54 along an arm axis that intersects the central hole axis 33 of a respective aligned one of the fixation holes 32 of the array 50. The respective aligned one of the fixation holes 32 of the first arm 58a can be adjacent to the respective aligned one of the fixation holes 32 of the second arm 58b along the array 50.

Referring to FIG. 3F, the inner surface 22 at the arms 58 can be recessed toward the outer surface 24 with respect to the inner surface 22 at each of the fixation nodes 54 and the fixation hub 28. Thus, as will be described in more detail below, the inner surface 22 at the fixation hub 28 and the nodes 54 can be configured to abut the underlying bone 21, while the arms 58 remain spaced from the underlying bone 21. Further, the inner surface 22 of the bone plate 20 can be planar. The outer surface 24 of the bone plate 20 can be rounded. Referring again to FIGS. 3A-3B, the first and second arms 58a and 58b of each pair of arms 58 can cooperate with the fixation hub 28 so as to define a respective aperture 60 that extends through the fixation body 26. Thus, the apertures 60 can extend through the fixation body 26 at a location radially between the fixation nodes 54 and the fixation hub 28. The apertures 60 can be referred to as outer apertures. The apertures 52 can be referred to as inner apertures.

The apertures 60 can be sized greater than the fixation holes 32. For instance, the apertures 60 can be sufficiently sized so as to define visualization windows that allow for visibility of the underlying patella. For instance, the user can visualize the patella through the visualization windows both as the bone plate 20 is being placed onto the patella, and after the bone plate 20 has been placed onto the patella. Thus, the surgeon can visually align the fixation holes 32 with respective bone fragments to which the bone plate 20 is to be secured. The apertures 60 can further assist in the malleability of the bone plate 20, which allows the bone plate 20 to be bent as desired so as to better conform to the patella. Further, the apertures 60 can define herniation holes that allow for soft tissue to herniate through the apertures 60. For instance, when the bone plate 20 is placed against the patella and secured to the patella, soft tissue residing between the patella bone and the bone plate 20 can herniate through the apertures 60, thereby reducing the profile of the bone plate 20 with respect to the epidermis.

The fixation nodes 54 of at least one first pair of adjacent fixation nodes 54 can be spaced circumferentially from each other a first distance, and the fixation nodes 54 of at least one second pair of adjacent fixation nodes 54 can be spaced circumferentially from each other a second distance that is different than the first distance. For instance, the second distance can be greater than the first distance. The at least one first pair of adjacent fixation nodes 54 can be defined by all pairs of adjacent fixation nodes 54, with respect to a single pair that defines the second pair of adjacent fixation nodes 54. The fixation nodes 54 of the second pair can be the inferior-most fixation nodes 54 of the bone plate 20 when the bone plate 20 is secured to the patella 23. It should be appreciated that the nodes 54 can be arranged about the fixation hub 28 in any manner as desired. For instance, the second distance can be equal to the first distance. Thus, in one example, the fixation nodes 54 can be equidistantly spaced circumferentially about the fixation hub 28. While the bone plate 20 can include six fixation nodes 54, it should be appreciated that the bone plate 20 can include any number of fixation nodes 54 as desired. For instance, the bone plate 20 can include more than six fixation nodes 54. Alternatively, the bone plate 20 can include fewer than six fixation nodes 54.

Referring now to FIGS. 3A-3D, and as described above, the bone plate 20 can further include at least one fixation leg 29, such as a plurality of fixation legs 29, that extends out from the fixation body 26. Each of the fixation legs 29 can include at least one fixation hole 32. Thus, each of the fixation legs 29 can be configured to secure to the patella 23 or one or more bone fragments of the patella 23 as desired. The fixation legs 29 can include a first fixation leg 62 that is configured to be secured to an inferior medial aspect of the patella 23. Thus, in one example, the first fixation leg 62 can be referred to as an inferior medial fixation leg. The first fixation leg 62 can extend both inferiorly and medially from the fixation body 26, and thus can be configured to secure to an inferior medial aspect of the patella 23. The fixation legs 29 can further include a second fixation leg 64 that is configured to be secured to an inferior lateral aspect of the patella 23. Thus, the second fixation leg 64 can be referred to as an inferior lateral fixation leg. The second fixation leg 64 can extend both inferiorly and laterally from the fixation body 26, and thus can be configured to secure to a lateral inferior aspect of the patella 23. The fixation legs 29 can further include a third fixation leg 66 that is configured to be secured to the inferior pole of the patella 23. Thus, the third fixation leg 66 can be referred to as an inferior fixation leg 66 in certain examples. The third fixation leg 66 can be circumferentially disposed between the first and second fixation legs 62 and 64. The hub, the nodes, and the legs 62-66 can all be monolithic with each other so as to define a single unitary structure. It should be appreciated that the at least one fixation leg 29 can include one or more up to all of the first, second, and third fixation legs 62-66. Thus, reference to the second leg 64 does not necessarily imply that the bone plate 20 includes the first leg 62. Further, reference to the third leg 66 does not necessarily imply that the bone plate 20 includes the first and second legs 62 and 64, respectively.

It should be appreciated that the bone plate 20 can be configured to be secured to the patella of a patent's right knee or a patient's left knee. In this regard, it should be appreciated that the medial fixation leg when the bone plate 20 is secured to the patella of a patient's right knee becomes the lateral fixation leg when the bone plate 20 is secured to the patella of a patient's left knee. Similarly, the lateral fixation leg when the bone plate 20 is secured to the patella of a patient's right knee becomes the medial fixation leg when the bone plate 20 is secured to the patella of a patient's left knee. Thus, reference to the medial fixation leg 62 and the lateral fixation leg 64 is by way of example only, it being appreciated that the medial fixation leg 62 and the lateral fixation leg 64 can be reversed.

The fixation legs 29 can extend from any location of the fixation body 26 as desired. In one example, the first fixation leg 62 can extend from a first one of the fixation nodes 54. The second fixation leg 64 can similarly extend from a second one of the fixation nodes 54. The first and second fixation nodes 54 can define the second pair of fixation nodes 54 described above. The third fixation leg 66 can extend from the fixation body 26 at a location between the first and second ones of the fixation nodes 54 of the second pair. In one example, the third fixation leg 66 can extend from an eyelet that defines one of the fixation holes 32 of the array 50. In particular, the third fixation leg 66 can extend from the eyelet that defines the inferior-most one of the fixation holes 32 of the array 50, and thus of the fixation hub 28. Thus, the third fixation leg 66 can be elongate along a respective central axis that intersects the central hole axis 33 of the inferior-most fixation hole 32 of the fixation hub 28. The first and second fixation legs 62 and 64 can extend from the fixation body 26 along respective central axes that are offset from the central hub axis 35. The third fixation leg 66 can extend from the fixation body 26 along a respective central axis that intersects the central hub axis 35.

The fixation legs 29 can define any number of fixation holes 32 as desired. In one example, the first fixation leg 62 can define first and second fixation holes 32 that are spaced from each other radially along the fixation leg 62. In particular, the first fixation leg 62 can support at least one medial eyelet 68 that defines a respective fixation hole 32. In one example, the at least one medial eyelet 68 can include first and second medial eyelets 68 that each defines a respective fixation hole 32. The first medial eyelet 68 can be disposed at a distal terminal end of the first fixation leg 62. Thus, the first medial eyelet 68 can also be referred to as a terminal medial eyelet 68. The fixation hole 32 defined by the first medial eyelet 68 can be referred to as a terminal fixation hole 32 The second medial eyelet 68 can be disposed between the fixation body 26 and the terminal end of the first fixation leg 62. Thus, the second medial eyelet 68 can be referred to as an intermediate medial eyelet 68. The fixation hole 32 defined by the second medial eyelet 68 can be referred to as an intermediate medial fixation hole 32. It should be appreciated that the first fixation leg 62 can include any number of intermediate medial eyelets 68 as desired. The intermediate medial eyelets 68 can be spaced from each other along the respective first fixation leg 62. Alternatively, as illustrated in FIGS. 4A-4B, the at least one medial eyelet 68 can include only the first medial eyelet 68 and no other medial eyelets 68.

The second fixation leg 64 can also define first and second fixation holes 32 that are spaced from each other radially along the second fixation leg 64. In particular, the second fixation leg 64 can support at least one lateral eyelet 70 that defines a respective fixation hole 32. In one example, the at least one lateral eyelet 70 can include first and second lateral eyelets 70 that each defines a respective fixation hole 32. The first lateral eyelet 70 can be disposed at a distal terminal end of the second fixation leg 64. Thus, the first lateral eyelet 70 can also be referred to as a terminal lateral eyelet 70. The fixation hole 32 defined by the first lateral eyelet 70 can be referred to as a terminal fixation hole 32 The second lateral eyelet 70 can be disposed between the fixation body 26 and the terminal end of the second fixation leg 64. Thus, the second lateral eyelet 70 can be referred to as an intermediate lateral eyelet 70. The fixation hole 32 defined by the second lateral eyelet 70 can be referred to as an intermediate lateral fixation hole 32. It should be appreciated that the second fixation leg 64 can include any number of intermediate lateral eyelets 70 as desired. The intermediate lateral eyelets can be spaced from each other radially along the respective second fixation leg 64. Alternatively, as illustrated in FIGS. 4A-4B, the at least one lateral eyelet 70 can include only the first lateral eyelet 70 and no other lateral eyelets 70.

The third fixation leg 66 can also define first and second fixation holes 32 that are spaced from each other radially along the third fixation leg 66. In particular, the third fixation leg 66 can support at least one inferior eyelet 72 that defines a respective fixation hole 32. In one example, the at least one inferior eyelet 72 can include first and second inferior eyelets 72 that each defines a respective fixation hole 32. The first inferior eyelet 72 can be disposed at a distal terminal end of the third fixation leg 66. Thus, the first inferior eyelet 72 can also be referred to as a terminal inferior eyelet 72. The fixation hole 32 defined by the first inferior eyelet 72 can be referred to as a terminal fixation hole 32. The second inferior eyelet 72 can be disposed between the fixation body 26 and the terminal end of the third fixation leg 66. Thus, the second inferior eyelet 72 can be referred to as an intermediate inferior eyelet 72. The fixation hole 32 defined by the second inferior eyelet 72 can be referred to as an intermediate inferior fixation hole 32. It should be appreciated that the third fixation leg 66 can include any number of intermediate inferior eyelets 72 as desired. The intermediate inferior eyelets 72 can be spaced from each other radially along the respective third fixation leg 66. Alternatively, as illustrated in FIGS. 4A-4B, the at least one inferior eyelet 68 can include only the first inferior eyelet 72 and no other inferior eyelets 72.

In this regard, referring to FIGS. 4A-4B, it should be appreciated the bone plate 20 can be constructed with shorter fixation legs 29 than those illustrated in FIGS. 3A-3E. Otherwise stated, the at least one of the first, second and third fixation legs 62-66 of the bone plate 20 illustrated in FIGS. 4A-4B can be shorter than a corresponding at least one of the first, second and third fixation 62-66 the bone plate 20 illustrated in FIGS. 3A-3F. Thus, as will be appreciated with respect to the description of FIGS. 9A-9E below, a surgeon can select the bone plate illustrated in FIGS. 3A-3F if additional positional flexibility for the bone anchors is desired along the fixation legs 29. Alternatively or additionally, the surgeon can select the bone plate illustrated in FIGS. 3A-3F if additional length of at least one of the fixation legs 29 is desired. Additional length can be desired to allow the bone anchor to be driven into one of the bone fragments. Alternatively or additionally, additional length of at least one or more of the fixation legs 29 may be desired in order to bend the one or more fixation legs 29 in such a manner so as to cradle and compress the bone fragments against each other. The fixation body 26 of the bone plate 20 illustrated in FIGS. 4A-4B can be as described with respect to the bone plate illustrated in FIGS. 3A-3F. Thus, the description of the fixation body 26 with respect to FIGS. 3A-3F can apply equally to the fixation body 26 illustrated in FIGS. 4A-4B.

Alternatively still, referring to FIGS. 5A-5B, the bone plate 20 can be constructed without one or more of the fixation legs 29 up to all of the fixation legs 29. Thus, as will be appreciated with respect to the description of FIGS. 9A-9E below, a surgeon can select the bone plate 20 illustrated in FIGS. 5A-5B if it is not desired to secure the bone plate to the inferior aspect of the patella 23. The fixation body 26 of the bone plate 20 illustrated in FIGS. 5A-5B is the same as the fixation body 26 illustrated and described above with respect to the bone plate 20 illustrated in FIGS. 3A-3F. Thus, the description of the fixation body 26 with respect to FIGS. 3A-3F can apply equally to the fixation body 26 illustrated in FIGS. 5A-5B. In one example, the outer surface 24 of the bone plate 20 illustrated in FIGS. 5A-5B can define an open area that is a percentage of an overall area of the outer surface 24. The overall area of the outer surface 24 can be measured by determining the area of the outer surface 24 when the bone plate 20 does not include any of the fixation holes 32, apertures 52, and apertures 60. Thus, the overall area of the outer surface 24 can be calculated when an entirety of the outer surface is continuous and uninterrupted. The actual area of the outer surface 24 of the bone plate 20 can be determined including all disruptions. The disruptions can be defined by the fixation holes 32, the apertures 52, and the apertures 60. The actual area can be subtracted from the overall area to determine the open area of the outer surface 24. The open area can be a percentage of the overall area. For instance, the percentage can be in a range from 38% to 60%. In one example, the percentage can range from 40% to 50%. For instance, the percentage can be 43%+/−3%. Thus, as described above, the bone plate 20 can be malleable, and can include visualization windows and herniation windows while, at the same time, being sufficiently rigid. The bone plate 20 can be constructed to define any suitable overall area as desired. In one example, the overall area can be less than 1000 $mm^2$. For instance, the overall area can be between 200 $mm^2$ and 900 $mm^2$. In one example, the overall area can be between 300 $mm^2$ and 900 $mm^2$. For instance, the overall area can be between 400 $mm^2$ and 600 $mm^2$.

As illustrated in FIG. 3F, the inner surface 22 of the bone plate 20 at the first fixation leg 62 can be recessed toward the outer surface 24 with respect to the inner surface 22 at each of the at least one medial eyelet 68. Thus, as will be described in more detail below, the inner surface 22 at the at least one medial eyelet 68 can be configured to abut the underlying bone 21, while the inner surface 22 at the first fixation leg 62 remain spaced from the underlying bone 21. Further, the inner surface 22 of the bone plate 20 at the second fixation leg 64 can be recessed toward the outer surface 24 with respect to the inner surface 22 at each at least one lateral eyelet 70. Thus, as will be described in more detail below, the inner surface 22 at the at least one lateral eyelet 70 can be configured to abut the underlying bone 21, while the inner surface 22 at the second fixation leg 64 remains spaced from the underlying bone 21. Further, the inner surface 22 of the bone plate 20 at the third fixation leg 66 can be recessed toward the outer surface 24 with respect to the inner surface 22 at each at least one inferior eyelet 72. Thus, as will be described in more detail below, the inner surface 22 at the at least one inferior eyelet 72 can be configured to abut the underlying bone 21, while the inner surface 22 at the third fixation leg 66 remains spaced from the underlying bone 21.

The fixation legs 29 can extend tangential to the curvature of the dome shape of the fixation body 26 as illustrated in FIG. 3E. Further, the first, second, and third fixation legs 62, 64, and 66, respectively, can be circumferentially spaced from each other, thus, the first, second, and third fixation legs 62, 64, and 66 can all lie on respective different planes.

Figure 6A:
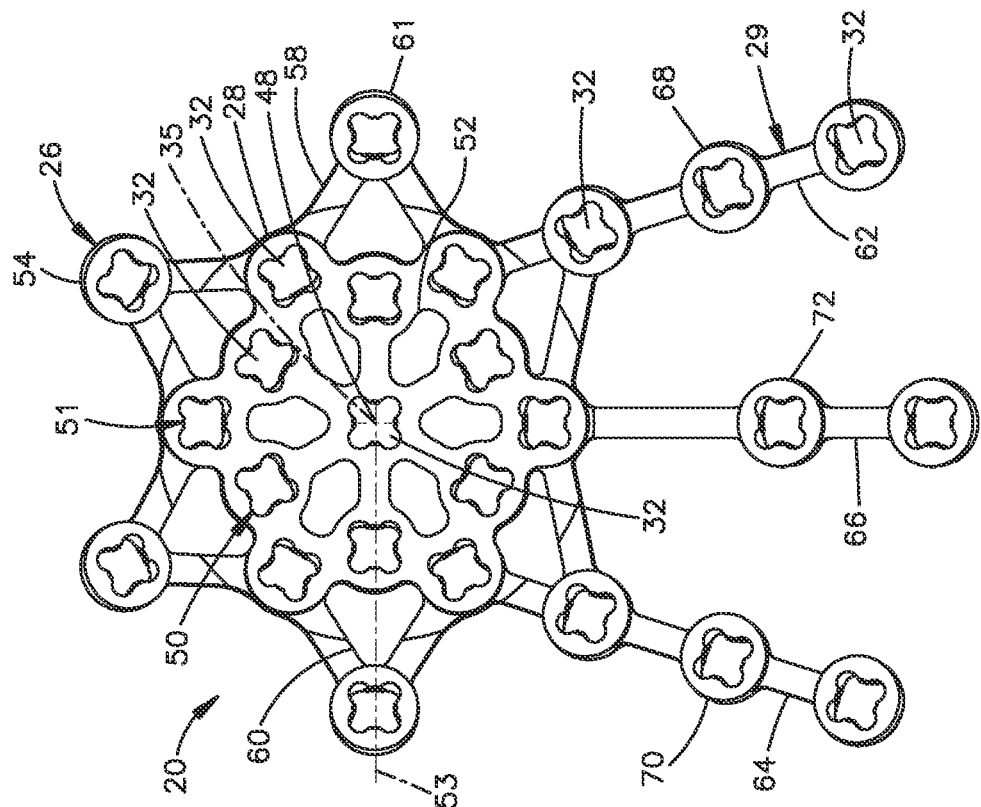
FIG. 6A is a top plan view of a bone plate similar to the bone plate illustrated in FIG. 5A, but showing the fixation body having additional fixation holes in one example.
Figure 6B:
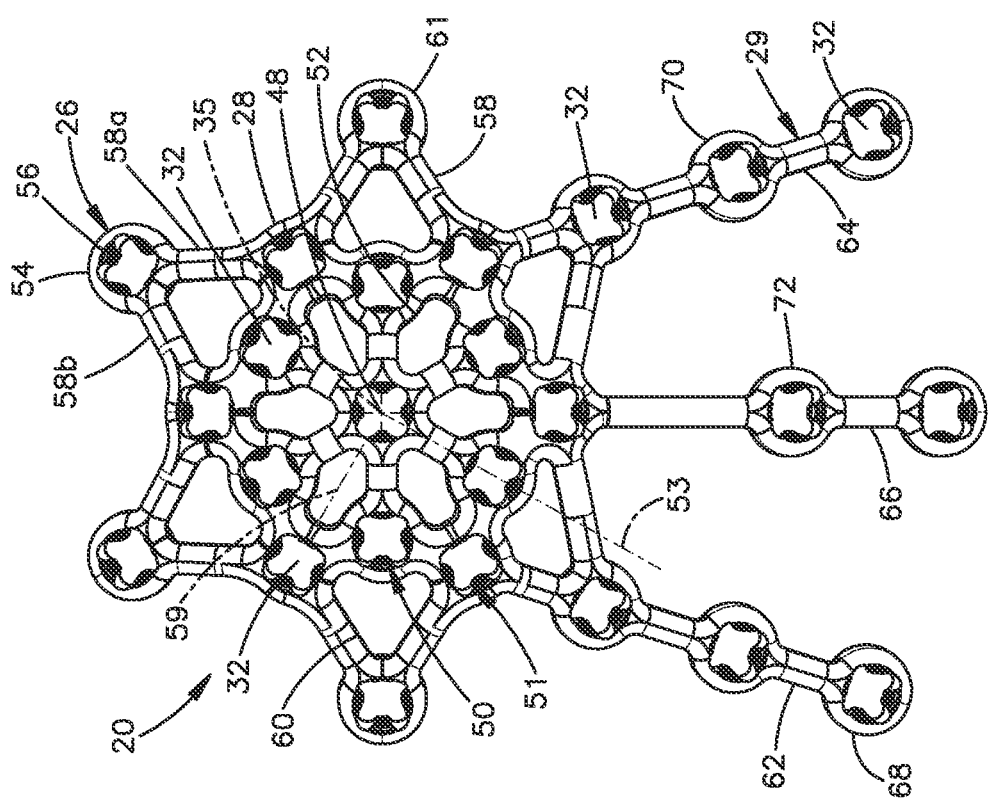
FIG. 6B is a bottom plan view of the bone plate illustrated in FIG. 6A.

Referring now to FIGS. 6A-6B, the bone plate 20 can be configured as described above with respect to FIGS. 3A-3F. However, in FIGS. 6A-6B, the fixation hub 28 can include first and second arrays 50 and 51 of fixation holes 32. In this regard, the array 50 of fixation holes 32 described above with respect to the bone plate 20 illustrated in FIGS. 3A-3F can be referred to as a first array 50 of fixation holes. As illustrated in FIGS. 6A-6B, the fixation hub 28 can include the second array 51 of fixation holes 32. Thus, the fixation hub 28 of the bone plate 20 illustrated in FIGS. 6A-6B can be sized larger than the fixation hub 28 of the bone plate 20 illustrated in FIGS. 3A-5B so as to include the first and second arrays 50 and 51 of fixation holes 32. Further, because the bone plate 20 illustrated in FIGS. 6A-6B includes the additional second array 51 of fixation holes 32, the bone plate 20 illustrated in FIGS. 6A-6B can allow for fixation to bone fragments at additional locations with respect to the bone plate 20 illustrated in FIGS. 3A-5B having only the single array 50 of fixation holes 32.

The second array 51 can be configured as a circumferential array. Thus, the second array can surround the geometric center 48 of the hub 28. The fixation holes 32 of the second array 51 can be offset radially outward with respect to the fixation holes 32 of the first array 50. For instance, the respective hole axes of the fixation holes 32 of the first array 50 can be spaced from the central hub axis 35 a first distance, and the respective hole axes of the fixation holes 32 of the second array 51 can be spaced from the central hub axis 35 a second distance that is greater than the first distance. Thus, the first array 50 of fixation holes 32 can be referred to as an inner array, and the second array 51 of fixation holes 32 can be referred to as an outer array. The first array 50 of fixation holes can be constructed as described above with respect to the bone plate illustrated in FIGS. 3A-5B.

The fixation holes 32 of the second array 51 can be arranged along a path that extends about the geometric center 48. For instance, the path of the second array can be a closed path that surrounds the geometric center 48. In one example, the path of the second array 51 can define a second circle. The central hub axis 35 can define the center of the second circle. Thus, the second circle can be concentric with the circle defined by the central hole axes 33 of the fixation holes 32 of the first array 50. The circle defined by the central hole axes 33 of the fixation holes 32 of the first array 50 can be referred to as a first circle. The first circle can be can be disposed between the second circle and the central hub axis 35. The central hole axes 33 (see FIG. 2B) of the fixation holes 32 of the second array 51 can lie on the second circle.

In one example, the fixation holes 32 of the second array 51 can be spaced equidistantly from each other along the second circle. Alternatively, the fixation holes 32 can be spaced at variable distances from each other. Further, while the fixation holes 32 of the second array 51 can be arranged on the circular path, it should be appreciated that the fixation holes 32 of the second array 51 can be alternatively arranged as desired. For instance, the fixation holes 32 of the second array 51 can lie on any curved path. The curved path can define an ellipse in one example. Alternatively, the path can define a polygon. For instance, the central hole axes 33 of the fixation holes of the second array 51 can define the vertices, respectively, of the polygon. In one example, as illustrated in FIGS. 5A-5B, the polygon can be a regular polygon. Alternatively, the polygon can be an irregular polygon.

In one example, the second array 51 can include six fixation holes 32. Thus, the regular polygon can be configured as a hexagon. It should be appreciated, however, that the second array 51 can include any number of fixation holes 32 as desired. In one example, the fixation hole 32 at the geometric center 48 and the fixation holes 32 of the first and second arrays 50 and 51 can constitute all fixation holes 32 of the fixation hub 28. Alternatively, the fixation hub 28 can include at least one additional fixation hole 32 in addition to the fixation hole 32 at the geometric center 48 and the fixation holes 32 of the first and second arrays 50 and 51. The at least one additional fixation hole 32 can be disposed between the geometric center 48 and the array 50. Alternatively or additionally, the at least one additional fixation hole 32 can be disposed between the first array 50 and the second array 51. Alternatively or additionally still, the at least one additional fixation hole 32 can be disposed radially outward of the second array 51. Thus, the second array 51 can be disposed between the at least one additional fixation hole 32 and the geometric center 48.

The radially outer surfaces of the eyelets that define the fixation holes 32 of the first and second arrays 50 and 51 can define the outer perimeter of the fixation body 26. The radially outer surfaces of the eyelets that define the fixation holes 32 of the second array 51 can be offset radially outward (i.e., away from the central hub axis 35) with respect the radially outer surfaces of the eyelets that define the fixation holes 32 of the first array 50. Further, eyelets that define the fixation holes 32 of the first array 50 can be alternatingly arranged with the eyelets that define the fixation holes 32 of the second array 51. Thus, each of the eyelets that define the fixation holes 32 of the first array 50 can be interconnected between adjacent ones of the eyelets that define the fixation holes 32 of the second array 51. Further, each of the eyelets that define the fixation holes 32 of the second array 51 can be interconnected between adjacent ones of the eyelets that define the fixation holes 32 of the first array 50.

The apertures 52 can be positioned circumferentially offset with respect to the fixation holes 32 of the first array 50. For instance, the straight lines 53 that intersect each of the central hub axis 35 and the central hole axes of respective ones of the fixation holes 32 of the first array 50 do not intersect the apertures 52 with respect to a top or bottom plan view of the bone plate 20. That is, the straight lines 53 can be circumferentially offset from the apertures 52. For instance, the straight lines 53 can be circumferentially equidistantly spaced from adjacent ones of the apertures 52.

Further, the apertures 52 can be elongate along the radial direction. Thus, in one example, the central axes 59 of the apertures 52 can intersect the central hub axis 35. Further, the central axes 59 of the apertures 52 can intersect the central hole axis of a respective aligned one of the fixation holes 32 of the second array 51. Thus, the apertures 52 can be disposed radially between a respective one of the fixation holes 32 of the second array and the geometric center of the hub 28. Further, the apertures 52 can be disposed between adjacent ones of the fixation holes 32 of the first array 50 with respect to the circumferential direction. Accordingly, straight lines 76 can pass through the central hub axis 35, the central hole axis 33 of a respective one of the fixation holes 32 of the second array 51, and can be coincident with the central axis 59 of a respective one of the apertures 52 with respect to a top or bottom plan view of the bone plate. The apertures 52 can be define any suitable shape as desired. In one example, the apertures 52 can define the shape of an arrow that points toward the geometric center 48. Further, the apertures 52 can span a majority of the radial distance from a respective aligned one of the fixation holes 32 of the second array 51 and the fixation hole 32 at the geometric center 48.

The geometric centers of the apertures 52 can lie on a respective circle that surrounds the geometric center 48 of the hub 28. For instance, the geometric center 48 of the hub 28 can define the center of the circle defined by the geometric centers of the apertures 52. Thus, the circle defined by the geometric centers of the apertures 52 can be concentric with each of the first and second circles. Further, in one example, the first circle can be disposed between the circle defined by the geometric centers of the apertures 52 and the second circle.

With continuing reference to FIGS. 6A-6B, and as described above, the fixation body 26 can include the plurality of fixation nodes 54 that are connected to the hub 28. In particular, the fixation body 26 includes at least one arm 58, such as a plurality of arms 58, that extends radially outward from the fixation hub 28 to a respective at least one of the fixation nodes 54. Thus, each of the fixation nodes 54 can be attached to the fixation hub 28 by the respective arms 58. For instance, the at least one arm 58 can extend to the outer surface 61 of the eyelet 56. In one example, the at least one arm 58 can include at least one pair of arms 58 that includes first and second arms 58a and 58b. Thus, each of the fixation nodes 54 can be secured to the fixation hub 28 by a respective pair of arms 58. Each pair of arms 58 can be defined by a first arm 58a and a second arm 58b. The arms 58a and 58b of each pair can converge toward each other as they extend from the fixation hub 28 to the respective one of the fixation nodes 54. Further, each of the arms 58 can extend from the fixation hub 28 to the respective one of the nodes 54 along a arm axis that intersects the central hole axis 33 of a respective aligned one of the fixation holes 32 of the second array 51. The respective aligned one of the fixation holes 32 of the first arm 58a can be adjacent to the respective aligned one of the fixation holes 32 of the second arm 58b along the array 50.

Further, the first and second arms 58a and 58b of each pair of arms 58 can cooperate with the fixation hub 28 so as to define a respective aperture 60 that extends through the fixation body 26. Thus, the apertures 60 can extend through the fixation body 26 at a location radially between the fixation nodes 54 and the fixation hub 28. The apertures 60 can be referred to as outer apertures. The apertures 52 can be referred to as inner apertures. The outer apertures 60 can be defined by a respective one of the nodes 54, a respective pair of adjacent eyelets that defines respective fixation holes 32 of the second array 51, and a respective one of the eyelets that defines the fixation hole 32 of the first array 50. The respective one of the eyelets that defines the fixation hole 32 of the first array 50 is interconnected between the adjacent eyelets of the respective pair of eyelets that defines the respective fixation holes 32 of the second array.

Further still, the bone plate illustrated in FIGS. 6A-6B can include at least fixation leg 29 in the manner described above with respect to FIGS. 3A-3F. Thus, the description of the legs 62-66 above with respect to FIGS. 3A-3F can apply to the fixation legs 62-66 illustrated in FIGS. 6A-6B unless otherwise indicated. The at least one fixation leg 29 can include the first fixation leg 62 that is configured to be secured to a medial aspect of the patella 23, the second fixation leg 64 that is configured to be secured to a lateral aspect of the patella 23, and the third fixation leg 66 that is configured to be secured to the inferior pole of the patella 23. The fixation legs 29 can extend from any location of the fixation body 26 as desired. In one example, the first fixation leg 62 can extend from a first one of the fixation nodes 54. The second fixation leg 64 can similarly extend from a second one of the fixation nodes 54. The third fixation leg 66 can extend from the fixation body 26 at a location between the first and second ones of the fixation nodes 54. In one example, the third fixation leg 66 can extend from an eyelet that defines one of the fixation holes 32 of the second array 51. In particular, the third fixation leg 66 can extend from the eyelet that defines the inferior-most one of the fixation holes 32 of the second array 51, and thus of the fixation hub 28. Thus, the third fixation leg 66 can be elongate along a respective central axis that intersects the central hole axis of the inferior-most fixation hole 32 of the fixation hub 28. The inferior-most one of the fixation holes 32 of the second array 51 can be interconnected between the first and second ones of the fixation nodes 54.

Referring now to FIGS. 6A-8B generally, the fixation legs 29 can define any number of fixation holes 32 as desired. In one example illustrated in FIGS. 6A-6B, the first fixation leg 62 can define first and second fixation holes 32 that are spaced from each other radially along the fixation leg 62. In particular, the first fixation leg 62 can support at least one medial eyelet 68 that defines a respective fixation hole 32. In one example, the at least one medial eyelet 68 can include first and second medial eyelets 68 that each defines a respective fixation hole 32. The first medial eyelet 68 can be disposed at a distal terminal end of the first fixation leg 62. Thus, the first medial eyelet 68 can also be referred to as a terminal medial eyelet 68. The fixation hole 32 defined by the first medial eyelet 68 can be referred to as a terminal fixation hole 32 The second medial eyelet 68 can be disposed between the fixation body 26 and the terminal end of the first fixation leg 62. Thus, the second medial eyelet 68 can be referred to as an intermediate medial eyelet 68. The fixation hole 32 defined by the second medial eyelet 68 can be referred to as an intermediate medial fixation hole 32. It should be appreciated that the first fixation leg 62 can include any number of intermediate medial eyelets 68 as desired. The intermediate medial eyelets 68 can be spaced from each other along the respective first fixation leg 62. Alternatively, as illustrated in FIGS. 7A-7B, the at least one medial eyelet 68 can include only the first medial eyelet 68 and no other medial eyelets 68.

The second fixation leg 64 can also define first and second fixation holes 32 that are spaced from each other radially along the second fixation leg 64. In particular, the second fixation leg 64 can support at least one lateral eyelet 70 that defines a respective fixation hole 32. In one example, the at least one lateral eyelet 70 can include first and second lateral eyelets 70 that each defines a respective fixation hole 32. The first lateral eyelet 70 can be disposed at a distal terminal end of the second fixation leg 64. Thus, the first lateral eyelet 70 can also be referred to as a terminal lateral eyelet 70. The fixation hole 32 defined by the first lateral eyelet 70 can be referred to as a terminal fixation hole 32 The second lateral eyelet 70 can be disposed between the fixation body 26 and the terminal end of the second fixation leg 64. Thus, the second lateral eyelet 70 can be referred to as an intermediate lateral eyelet 70. The fixation hole 32 defined by the second lateral eyelet 70 can be referred to as an intermediate lateral fixation hole 32. It should be appreciated that the second fixation leg 64 can include any number of intermediate lateral eyelets 70 as desired. The intermediate lateral eyelets can be spaced from each other radially along the respective second fixation leg 64. Alternatively, as illustrated in FIGS. 7A-7B, the at least one lateral eyelet 70 can include only the first lateral eyelet 70 and no other lateral eyelets 70.

The third fixation leg 66 can also define first and second fixation holes 32 that are spaced from each other radially along the third fixation leg 66. In particular, the third fixation leg 66 can support at least one inferior eyelet 72 that defines a respective fixation hole 32. In one example, the at least one inferior eyelet 72 can include first and second inferior eyelets 72 that each defines a respective fixation hole 32. The first inferior eyelet 72 can be disposed at a distal terminal end of the third fixation leg 66. Thus, the first inferior eyelet 72 can also be referred to as a terminal inferior eyelet 72. The fixation hole 32 defined by the first inferior eyelet 72 can be referred to as a terminal fixation hole 32. The second inferior eyelet 72 can be disposed between the fixation body 26 and the terminal end of the third fixation leg 66. Thus, the second inferior eyelet 72 can be referred to as an intermediate inferior eyelet 72. The fixation hole 32 defined by the second inferior eyelet 72 can be referred to as an intermediate inferior fixation hole 32. It should be appreciated that the third fixation leg 66 can include any number of intermediate inferior eyelets 72 as desired. The intermediate inferior eyelets 72 can be spaced from each other radially along the respective third fixation leg 66. Alternatively, as illustrated in FIGS. 7A-7B, the at least one inferior eyelet 68 can include only the first inferior eyelet 72 and no other inferior eyelets 72.

Figure 7B:
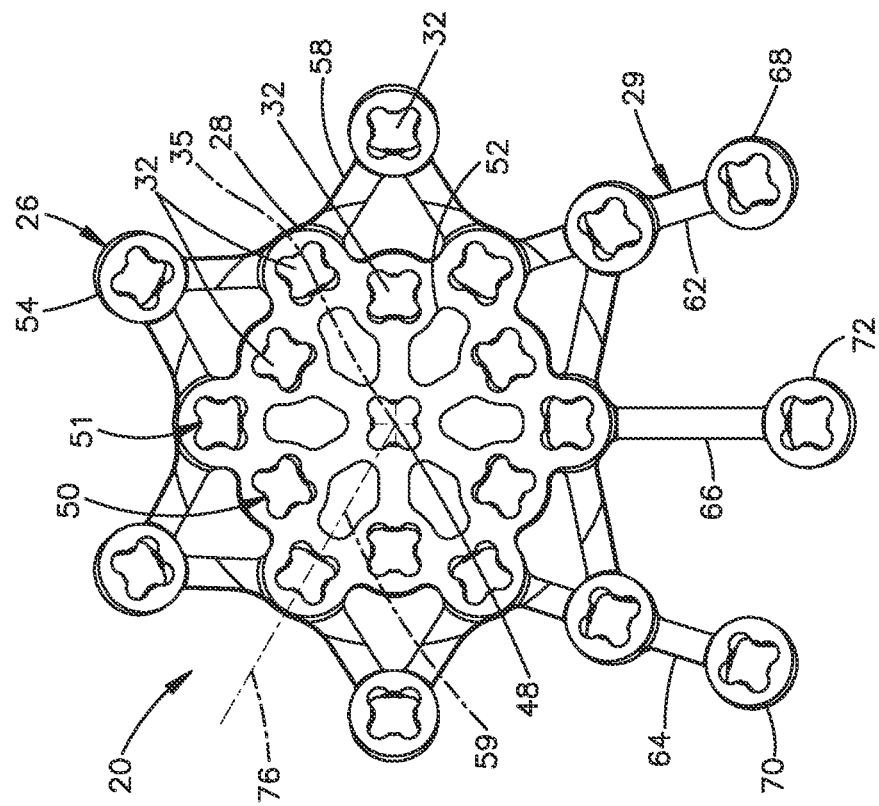
FIG. 7B is a bottom plan view of the bone plate illustrated in FIG. 7A.
Figure 7A:
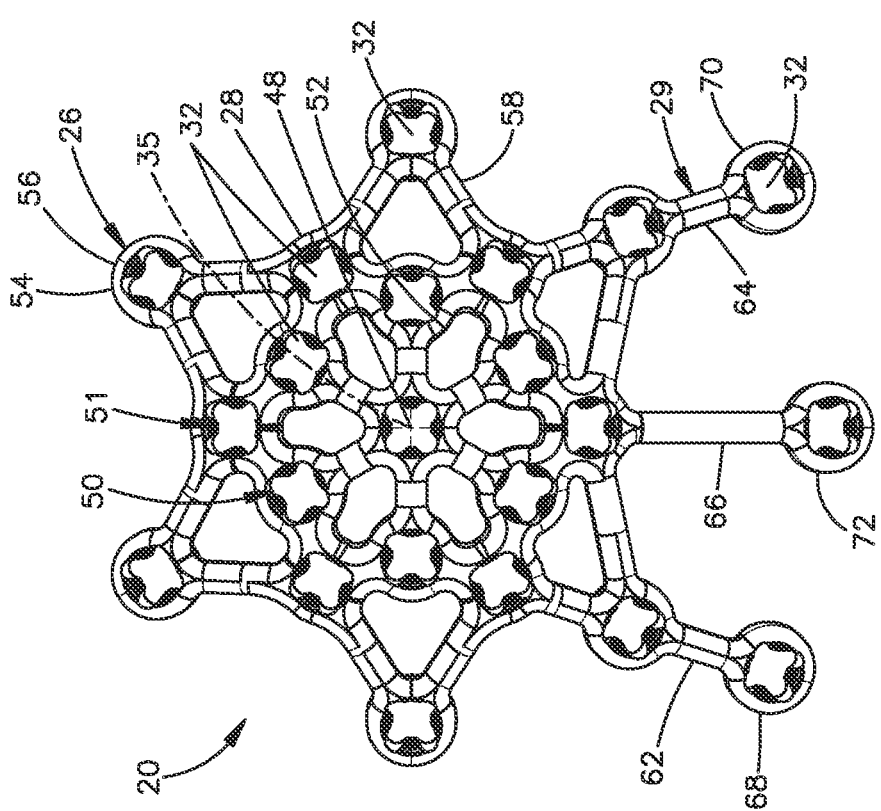
FIG. 7A is a top plan view of a bone plate similar to the bone plate illustrated in FIG. 6A but shown having shorter fixation legs.

In this regard, referring to FIGS. 7A-7B, it should be appreciated the bone plate 20 can be constructed with shorter fixation legs 29 than those illustrated in FIGS. 6A-6B. Otherwise stated, the at least one of the first, second and third fixation legs 62-66 of the bone plate 20 illustrated in FIGS. 7A-7B can be shorter than a corresponding at least one of the first, second and third fixation 62-66 the bone plate 20 illustrated in FIGS. 6A-6F. The fixation body 26 of the bone plate 20 illustrated in FIGS. 7A-7B can be as described with respect to the bone plate illustrated in FIGS. 6A-6B. Thus, the description of the fixation body 26 with respect to FIGS. 6A-6B can apply equally to the fixation body 26 illustrated in FIGS. 7A-7B.

Alternatively still, referring to FIGS. 8A-8B, the bone plate 20 can be constructed without one or more of the fixation legs 29 up to all of the fixation legs 29. Thus, the bone plate 20 can include the fixation body 26 including the fixation hub 28 and the fixation nodes 54, but no fixation legs 29. The fixation body 26 of the bone plate 20 illustrated in FIGS. 8A-8B is the same as the fixation body 26 illustrated and described above with respect to the bone plate 20 illustrated in FIGS. 6A-6B. Thus, the description of the fixation body 26 with respect to FIGS. 6A-6B can apply equally to the fixation body 26 illustrated in FIGS. 8A-8B. In one example, the outer surface 24 of the bone plate 20 illustrated in FIGS. 8A-8B can define an open area that is a percentage of an overall area of the outer surface 24. The overall area of the outer surface 24 can be measured by determining the area of the outer surface 24 when the bone plate 20 does not include any of the fixation holes 32, apertures 52, and apertures 60. Thus, the overall area of the outer surface 24 can be calculated when an entirety of the outer surface is continuous and uninterrupted. The actual area of the outer surface 24 of the bone plate 20 can be determined including all disruptions. The disruptions can be defined by the fixation holes 32, the apertures 52, and the apertures 60. The actual area can be subtracted from the overall area to determine the open area of the outer surface 24. The open area can be a percentage of the overall area. For instance, the percentage greater than 27%. For instance, the percentage can range from 27% to 65%. In one example, the percentage can range from 30% to 60%. For instance, the percentage can range from 40% to 60%. In one example, the percentage can be substantially 55%. Thus, as described above, the bone plate 20 can be malleable, and can include visualization windows and herniation windows while, at the same time, being sufficiently rigid. The bone plate 20 can be constructed to define any suitable overall area as desired. In one example, the overall area can be greater than 900 mm$^2$. For instance, the overall area can be greater than 1000 mm$^2$. In one example, the overall area can range from 900 mm$^2$ and 1500 mm$^2$. For instance, the overall area can range from 900 mm$^2$ to 1200 mm$^2$. For instance, the overall area can range from 900 mm$^2$ to 1100 mm$^2$.

Thus, referring to FIGS. 3A-8B in general, it can be said that the fixation body 26, and thus the bone plate 20, includes at least one array of fixation holes 32 that extend through the hub 28. The at least one array can include a single array 50 as illustrated in FIGS. 3A-5B. Alternatively, the at least one array can include first and second arrays 50 and 51 as illustrated in FIGS. 6A-8B. It should be appreciated, however, that the fixation body 26 can include any suitable number of arrays of fixation holes 32 that extend through the fixation hub 28 as desired. Further, it can be said that the bone plate 20 can include at least one fixation leg that extends from the fixation body 26. The at least one fixation leg can have a sufficient length to be bent around a peripheral rim of the patella as described in more detail below. For instance, the at least one fixation leg can include the first fixation leg 62, the second fixation leg 64, and the third fixation leg 66. The fixation legs 62-66 can define any number of fixation holes 32 as desired. For instance, in one example, the fixation legs 62-66 can define first and second fixation hole 32. In another example, the fixation legs 62-66 can define a single fixation hole 32.

In this regard, it should be appreciated that a kit of bone plates 20 can be provided. The kit can include at least one first bone plate 20 having a fixation body 26 with the single array 50 of fixation holes 32. The kit can include at least one second bone plate 20 having a fixation body with the first and second arrays 50 and 51 of fixation holes 32. The second bone plate can be sized larger than the first bone plate. The at least one first bone plate 20 can include bone plates 20 having the at least one fixation leg 29. Ones of the first bone plates 20 having the at least one fixation leg 29 can include different numbers of fixation holes 32 that extends through the at least one fixation leg. Alternatively or additionally, the at least one first bone plate 20 can include at least one bone plate 20 having no fixation legs 29. Similarly, the at least one second bone plate 20 can include bone plates 20 having the at least one fixation leg 29. Ones of the second bone plates 20 having the at least one fixation leg 29 can include different numbers of fixation holes 32 that extends through the at least one fixation leg. Alternatively or additionally, the at least one second bone plate 20 can include at least one bone plate 20 having no fixation legs 29.

A method of securing the fixation plate 20 to the underlying bone 21 will now be described with reference to FIGS. 9A-9D. In particular, the method can begin by creating an incision that exposes the anterior aspect of the patella 23. Thus, the bone plate 23 can be placed against the patella 23 along an anterior approach. As illustrated, the patella 23 is fractured and defines a plurality of patellar bone fragments 74. In instances where the patella 23 is severely comminuted, the bone fragments 74 can be compressed against each other thereby reducing the fracture using any suitable clamp or forceps. The bone plate 20 can then be placed against the underlying patella 23. The bone plate 20 can further be contoured so as to conform to the underlying patella 23. For instance, the bone plate body 26 can be contoured by bending one or more of the arms 58. One or more up to all of the legs 62-66 can also be bent so as to conform to the underlying patella 23. As described above, the inner surface 22 at the arms 58 can be recessed toward the outer surface 24 with respect to the inner surface 22 at each of the fixation nodes 54 and the fixation hub 28. Further, the inner surface at the legs 29 can be recessed toward the outer surface 24 with respect to the inner surface 22 at the eyelets that define the fixation holes 32 of the legs 29. Thus, the inner surface 22 at the arms 58 and the legs 29 can be spaced from the patella 23. The fixation hub 28, the fixation nodes 54, and the eyelets of the legs 29 (if present) can abut the patella 23.

In this regard, it should be appreciated that the apertures 52 of the bone plate 20 can assist in the malleability of the bone plate 20. Thus, the bone plate 20 can be bent as desired so as to conform to the underlying patella 23. The apertures 60 of the bone plate 20 of FIGS. 6A-8B can further assist in the malleability of the bone plate 20. Thus, the bone plate 20 can be bent in situ to conform to the outer surface of the patella 23. In particular, the fixation hub 28 can be bent as desired to better conform to the outer surface of the patella 23 than the preformed dome shape of the fixation hub 28. Further, the arms 58 can be bent out of plane. Out of plane bending can include a first inward direction toward the underlying bone. The inward direction can be generally defined as from the outer surface 24 to the inner surface 22. Out of plane bending can include a second outward direction away from the underlying bone. The outward direction can be generally defined as from the inner surface 22 to the inner outer surface 24. Alternatively or additionally, the arms 58 can be bent in-plane. That is, the arms 58 can be bent so as to not move further from or closer to the underlying patella while, at the same time, maintaining their respective angular orientations. Alternatively or additionally still, the arms 58 can further be twisted so as to adjust the angular orientation of the inner surface 22 at the eyelets that define the fixation holes 32 of the nodes 54. Thus, one or more of the arms 58 can be deformed so as to cause the inner surface 22 at the nodes 54 to better conform to the surface of the patella 23.

In one example, the arms 58 can be bent such that the fixation holes 32 of at least one of the nodes 54 can be aligned with the patellar rim. For instance, depending on the size of the bone plate 20 and the size of the patella 23, all of the nodes can extend at least to the patellar rim. Thus, the respective bone anchors 34 can be driven through the fixation holes 32 of at least one or more of the nodes 54 and into the patellar rim in a substantially posterior direction. In another example, at least one or more of the arms 58 can be bent such that the node 54 extends about the patellar rim. Thus, the respective bone anchor 34 can be driven through the fixation hole 32 of the node 54 substantially in a plane that is oriented substantially perpendicular to the posterior direction.

Further, one or more up to all of the legs 62-66 can be bent as desired to better conform to the outer surface of the patella 23. For instance, one or more up to all of the legs 62-66 can be bent out of plane. Alternatively or additionally, one or more up to all of the legs 62-66 can be bent out in plane. Alternatively or additionally still, one or more up to all of the legs 62-66 can be twisted so as to adjust the angular orientation of the inner surface 22 at the eyelets that define the fixation holes 32 of the nodes 54. Thus, one or more of the legs 62-66 can be deformed so as to cause the inner surface 22 at the one or more of the legs 62-66 to better conform to the surface of the patella 23.

Once the bone plate 20 has been placed against the patella 23 and bent as desired, the method can including the steps of driving bone anchors 34 into respective ones of the fixation holes 32 of the bone plate 20. For instance, the method can include the step of identifying fixation holes 32 of the bone plate 20 that are aligned with one or more bone fragments 74, such that driving a bone anchor 34 through the aligned fixation holes 32 will gain reliable purchase with the bone fragment 74. Next, the bone anchors 34 can be driven into the identified fixation holes 32. In this regard, it is appreciated that the fixation hub 28 can include one or more of the identified fixation holes 32. Alternatively or additionally, the fixation nodes 54 can include one or more of the identified fixation holes 32.

Figure 9B:
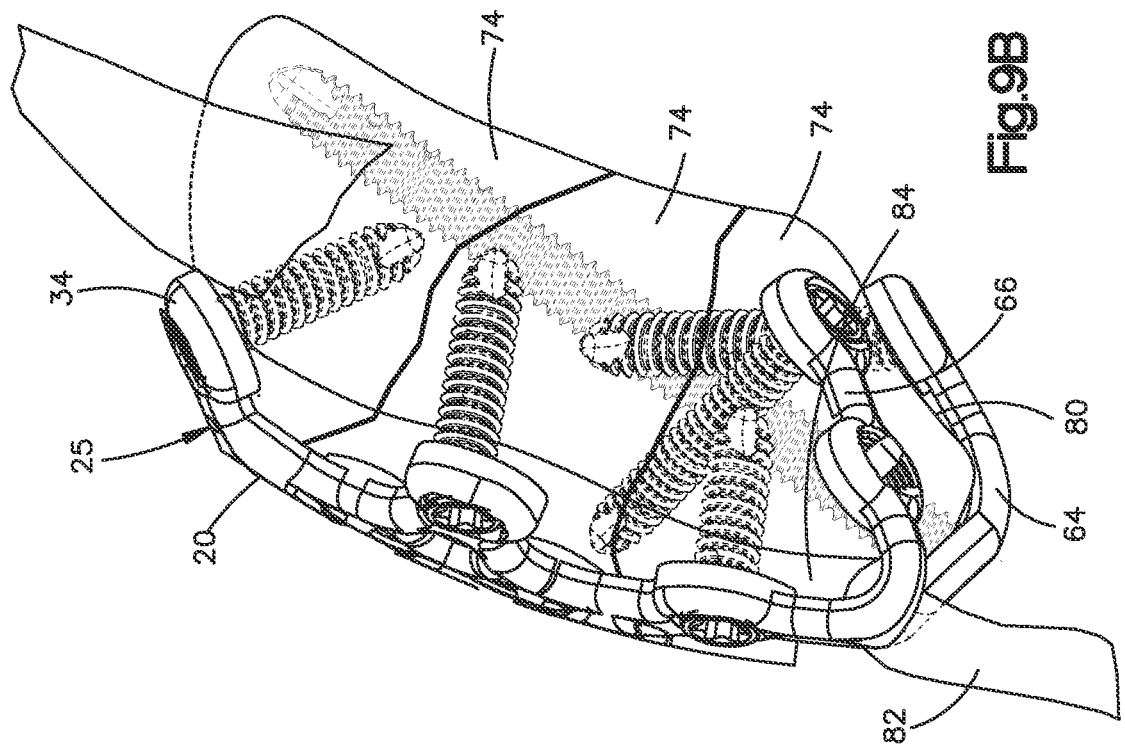
FIG. 9B is another side elevation view of the patella fixation assembly showing a second fixation leg secured to a lateral aspect of the fractured patella.
Figure 9A:
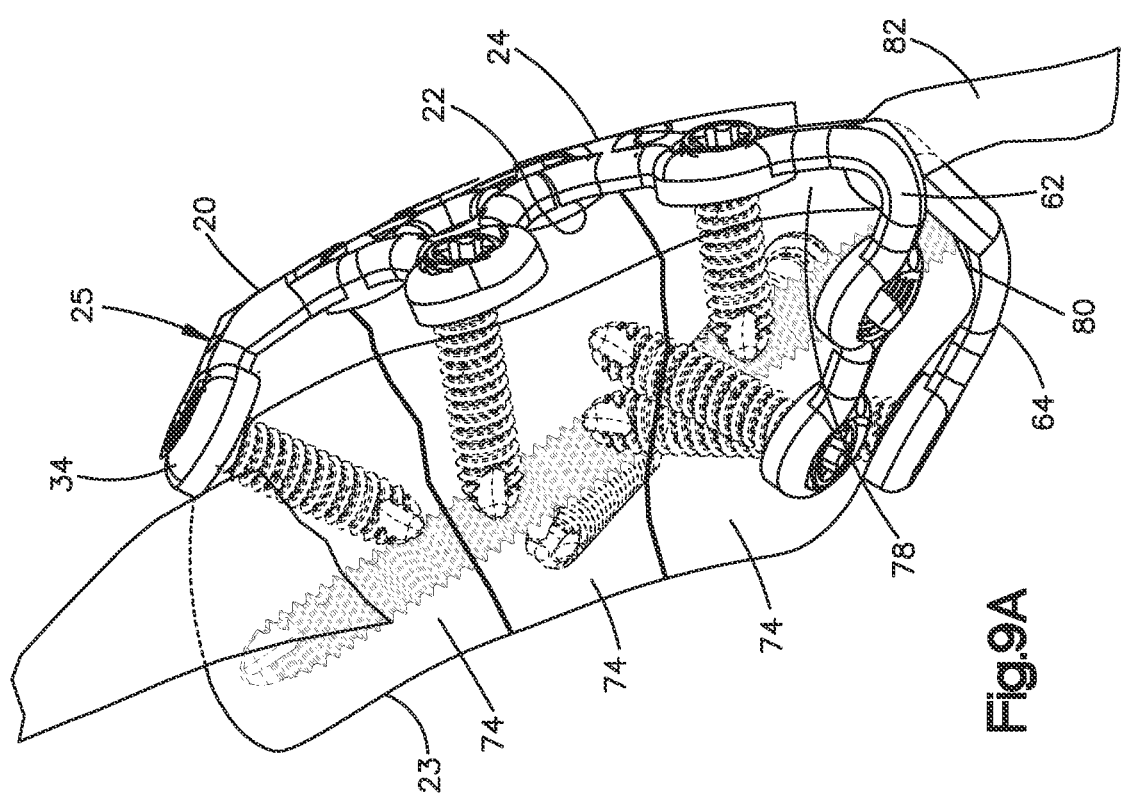
FIG. 9A is a side elevation view of the patella fixation assembly illustrated in FIG. 1A, showing a first fixation leg secured to a medial aspect of a fractured patella.

As illustrated in FIGS. 9A-9B, one of the bone anchors 34 can extend through the third fixation leg 66, through a near cortex to a far cortex opposite the near cortex. Thus, the bone anchor 34 can threadedly purchase with both the near cortex and the far cortex. In one example, the near cortex can be defined by the inferior pole of the patella 23, and the far cortex can be defined by the superior pole of the patella 23. As will be appreciated from the description below, it will be appreciated that the near cortex can alternatively be defined by the superior pole of the patella 23 and the far cortex can be defined by the inferior pole of the patella. Alternatively, the near cortex can be defined by the medial cortex of the patella 23 and the far cortex can be defined by the lateral cortex of the patella. Alternatively still, the near cortex can be defined by the lateral cortex of the patella 23 and the far cortex can be defined by the medial cortex of the patella.

It is further recognized that the inferior pole 80 of the patella 23 can often be comminuted, and can contain osteoporotic bone. In fact, inferior pole comminution has been observed in 88% of fractures of the patella 23. Accordingly, fixation of the bone plate 20 to the patella 23 can be augmented by suture fixation if desired. The method of fixation can further include the step of augmenting fixation of the bone plate 20 to the patella 23 by fixing at least one suture to the patellar tendon 82 and to the plate 20. In one example, the sutures can be configured as FiberWire® sutures commercially available from Arthrex, having a place of business in Naples, FL., though it should be appreciated that any suitable suture is envisioned. Thus, the method can include the step of attaching one or more sutures to the patellar tendon 82. The sutures can thus be included in the fixation system. In one example, the sutures can be stitched through the patellar tendon 82 in a Krackow configuration. The free end of the suture can then be passed over the plate in the inferior direction, and tied to the plate 20. For instance, the sutures can be inserted through respective ones of the apertures 52 and the apertures 60 (if present) so as to tie the bone plate 20 to the patellar tendon 82.

Figure 9C:
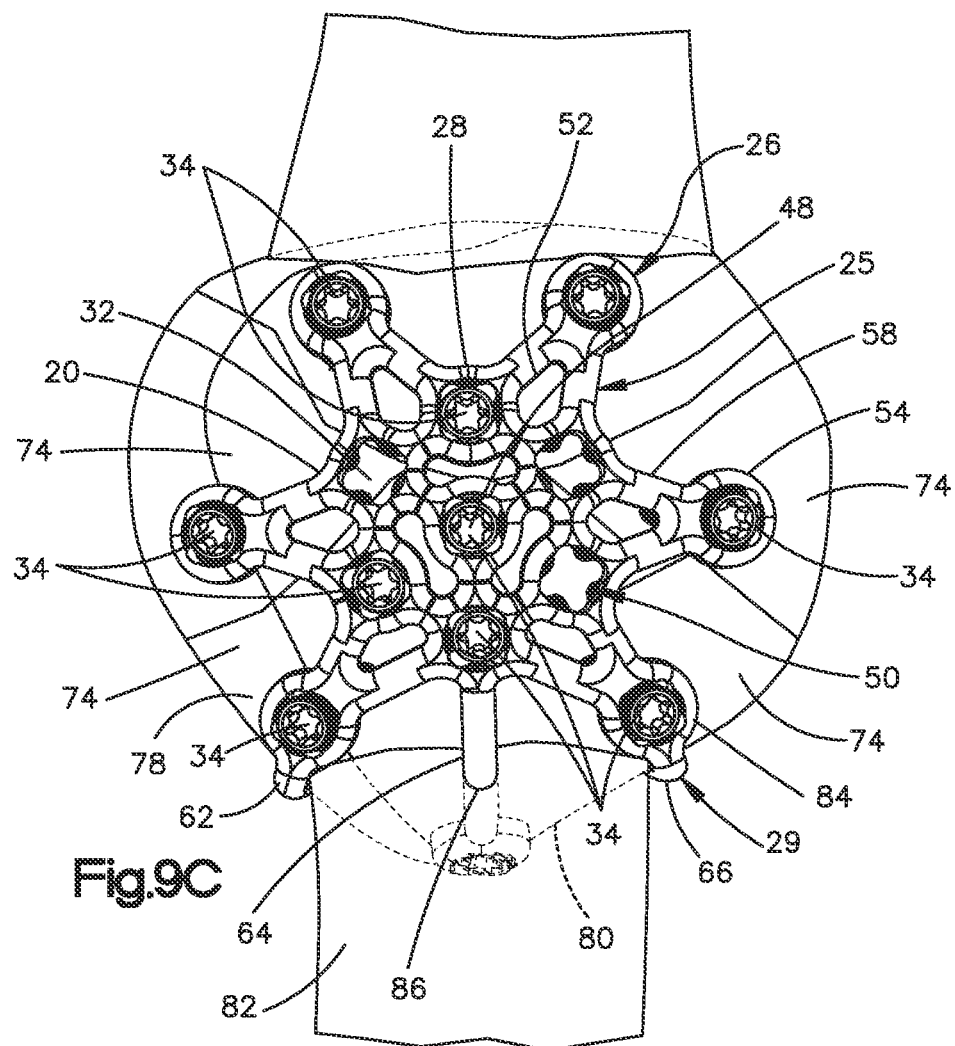
FIG. 9C is a top plan view of the patella fixation assembly showing an inferior fixation leg secured to an inferior pole of the fractured patella.
Figure 9D:
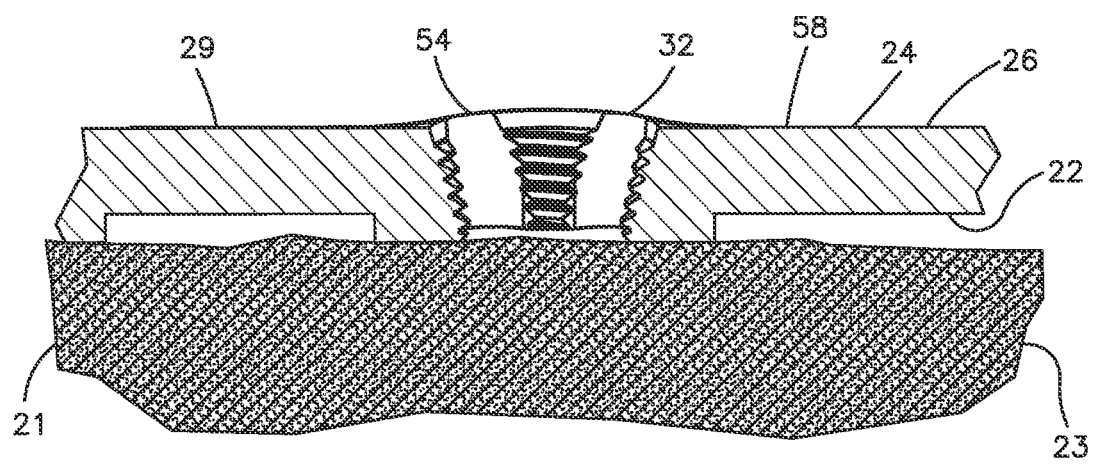
FIG. 9D is a sectional side elevation view of the bone plate as illustrated in FIG. 3F, shown secured to the patella.

In some examples, as illustrated in FIGS. 9A-9C, the bone plate 20 can include at least one leg 29 that extends from the fixation body 26. The at least one leg 29 (if present) can be deformed so as to cause the inner surface 22 at the at least one eyelet supported by the leg to better conform to the surface of the patella 23. For instance, the at least one leg 29 can be bent in plane, bent out of plane, and twisted as desired. Thus, the first or inferior medial leg 62 (if present) can be deformed so as to cause the inner surface 22 at the at least one medial eyelet 68 to abut the patella 23. In one example, the first leg 62 can have a length sufficient so as to extend around the medial inferior rim 78 of the patella 23. Thus, the first leg 62 can be deformed so as to cause the inner surface 22 at the at least one medial eyelet 68 to abut the patella 23. In one example, the first leg 62 can have a length sufficient so as to extend around the medial inferior rim 78 of the patella 23. The first leg 62 can be deformed such that the respective at least one fixation hole 32 can receive a bone anchor 34 that reliably secures the medial leg 62 to a bone fragment 74.

Further, the second or lateral leg 64 (if present) can be deformed so as to cause the inner surface 22 at the at least one lateral eyelet 70 to abut the patella 23. In one example, the second leg 64 can have a length sufficient so as to extend around the lateral inferior rim 84 of the patella 23. Thus, the second leg 64 can be deformed so as to cause the inner surface 22 at the at least one lateral eyelet 70 to abut the patella 23. In one example, the second leg 64 can have a length sufficient so as to extend around the lateral inferior rim 84 of the patella 23. The second leg 64 can be deformed such that the respective at least one fixation hole 32 can receive a bone anchor 34 that reliably secures the second leg 64 to a bone fragment 74.

Further, still, the third or inferior leg 66 (if present) can be deformed so as to cause the inner surface 22 at the at least one inferior eyelet 70 to abut the patella 23. In one example, the third leg 66 can have a length sufficient so as to extend around the inferior pole 80 of the patella 23. Thus, the third leg 66 can be deformed so as to cause the inner surface 22 at the at least one inferior eyelet 72 to abut the patella inferior pole 80. In one example, the third leg 66 can have a length sufficient so as to extend around the inferior pole 80. Further, an incision 86 can be made through the patellar tendon 82, and the third leg 66 can be inserted through the incision 86 so as to rest against the patella 23 at a position posterior of the patellar tendon 82. The third leg 66 can be deformed such that the respective at least one fixation hole 32 can receive a bone anchor 34 that reliably secures the third leg 66 to a bone fragment 74. It is further recognized that the first leg 62, the second leg 64, and the third leg 66 can all abut the inferior aspect of the patella 23 in different planes, thereby forming a cradle that maintains comminuted bone fragments compressed against adjacent bone fragments. Thus, the first leg 62, the second leg 64, and the third leg 66 can apply a compression force to the inferior aspect of the patella 23 that causes the bone fragments 74 to compress against each other, thereby facilitating healing.

Figure 9E:
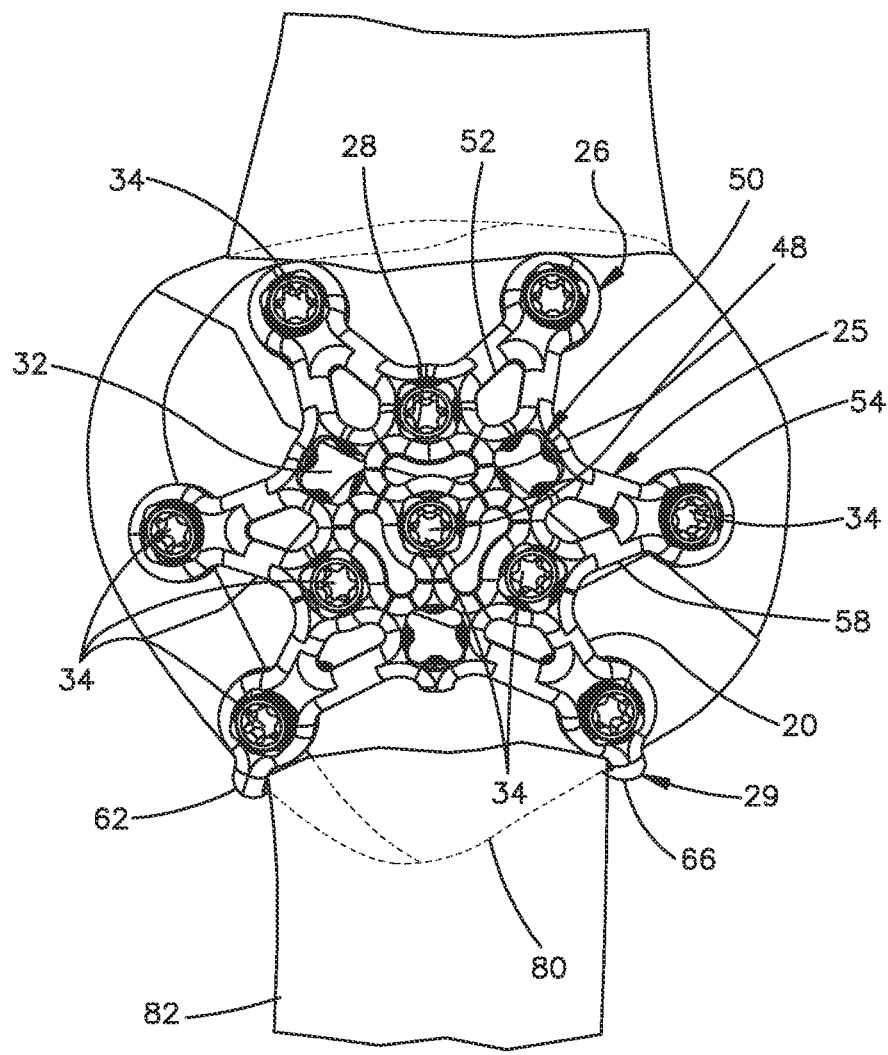
FIG. 9E is a top plan view of the patella fixation assembly similar to FIG. 9C, but showing the bone plate with the inferior fixation leg removed.

Referring now to FIG. 9E, it is recognized that some patella fractures do not involve comminutions at the inferior pole 80. Accordingly, in order to avoid creating unnecessary incisions in the patellar tendon 82, the bone plate 20 described above can include the first leg 62 and the second leg 64, but can lack the third leg 66. Alternatively, the third leg 66 can be removable from the fixation body 26. For instance, a cutting implement can sever the third leg 66 from the fixation body 26. Alternatively or additionally, the third leg 66 can define a weakened break-away region. The weakened break-away region can define a material thickness less than the material thickness at a remainder of the inferior leg. The break-away region can be immediately adjacent the fixation body 26 so as to eliminate potential irritating projections and sharp edges when the third leg 66 is removed. In this regard, any one or more up to all of the first, second, and third legs 62-66 can be removed from the bone plate 20 as desired.

Figure 10C:
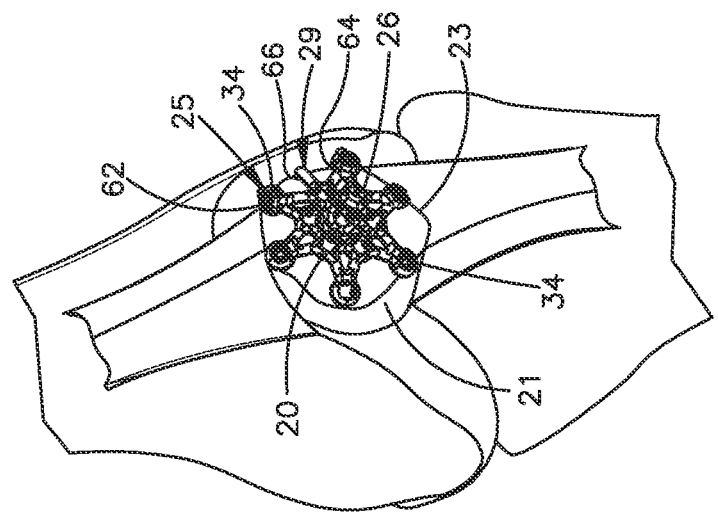
FIG. 10C is a perspective view of the patella fixation system illustrated in FIG. 10B, but showing the bone plate secured to the fractured patella in a still another different orientation.
Figure 10B:
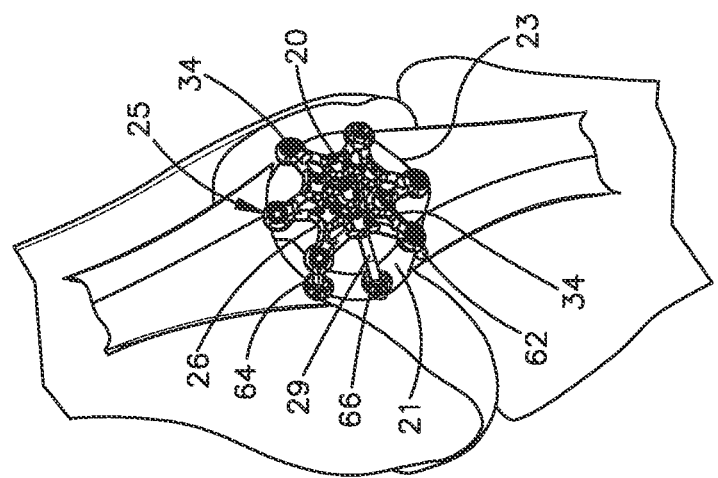
FIG. 10B is a perspective view of the patella fixation system illustrated in FIG. 10A, but showing the bone plate secured to the fractured patella in a another different orientation.
Figure 10A:
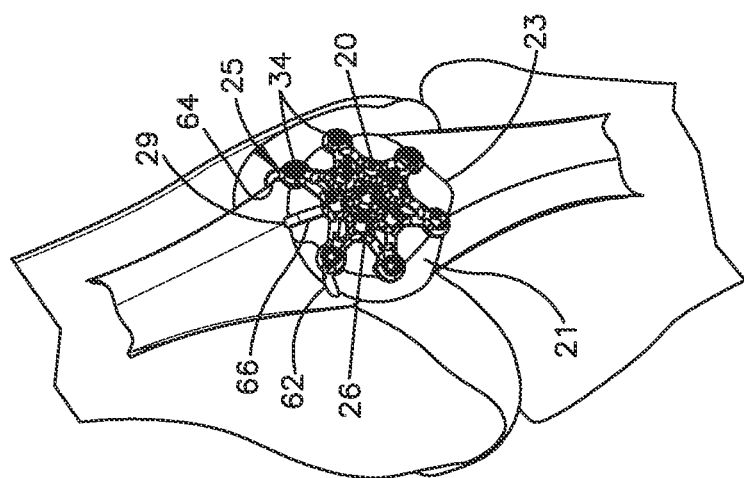
FIG. 10A is a perspective view of the patella fixation system illustrated in FIG. 1A, but showing the bone plate secured to the fractured patella in a different orientation.

As described above, the bone plate 20 can be oriented such that the at least one fixation leg 29 extend inferiorly from the fixation body 26. It should be appreciated, of course, that the bone plate 20 can be fixed to the patella 23 in any orientation as desired. For instance, referring to FIG. 10A, the bone plate 20 can be fixed to the patella 23 such that the at least one fixation leg 29 extends superiorly from the fixation body 26. Thus, the first fixation leg 62 can extend to a superior medial aspect of the patella 23. The second fixation leg 64 can extend to a superior inferior lateral aspect of the patella 23. The third fixation leg 66 can extend to the superior pole of the patella 23. Alternatively, referring to FIG. 10B, the bone plate 20 can be fixed to the patella 23 such that the at least one fixation leg 29 extends medially from the fixation body 26. Accordingly, the at least one fixation leg 29 can extend to the medial rim of the patella 23. For instance, the first fixation leg 62 can extend to an inferior aspect of the medial rim. The second fixation leg 64 can extend to a superior aspect of the medial rim. The third fixation leg 66 can extend to a central region of the medial rim. Alternatively still, referring to FIG. 10C, the bone plate 20 can be fixed to the patella 23 such that the at least one fixation leg 29 extends laterally from the fixation body 26. Accordingly, the at least one fixation leg 29 can extend to the lateral rim of the patella 23. For instance, the first fixation leg 62 can extend to a superior aspect of the lateral rim. The second fixation leg 64 can extend to an inferior aspect of the lateral rim. The third fixation leg 66 can extend to a central region of the lateral rim.

Figure 11:
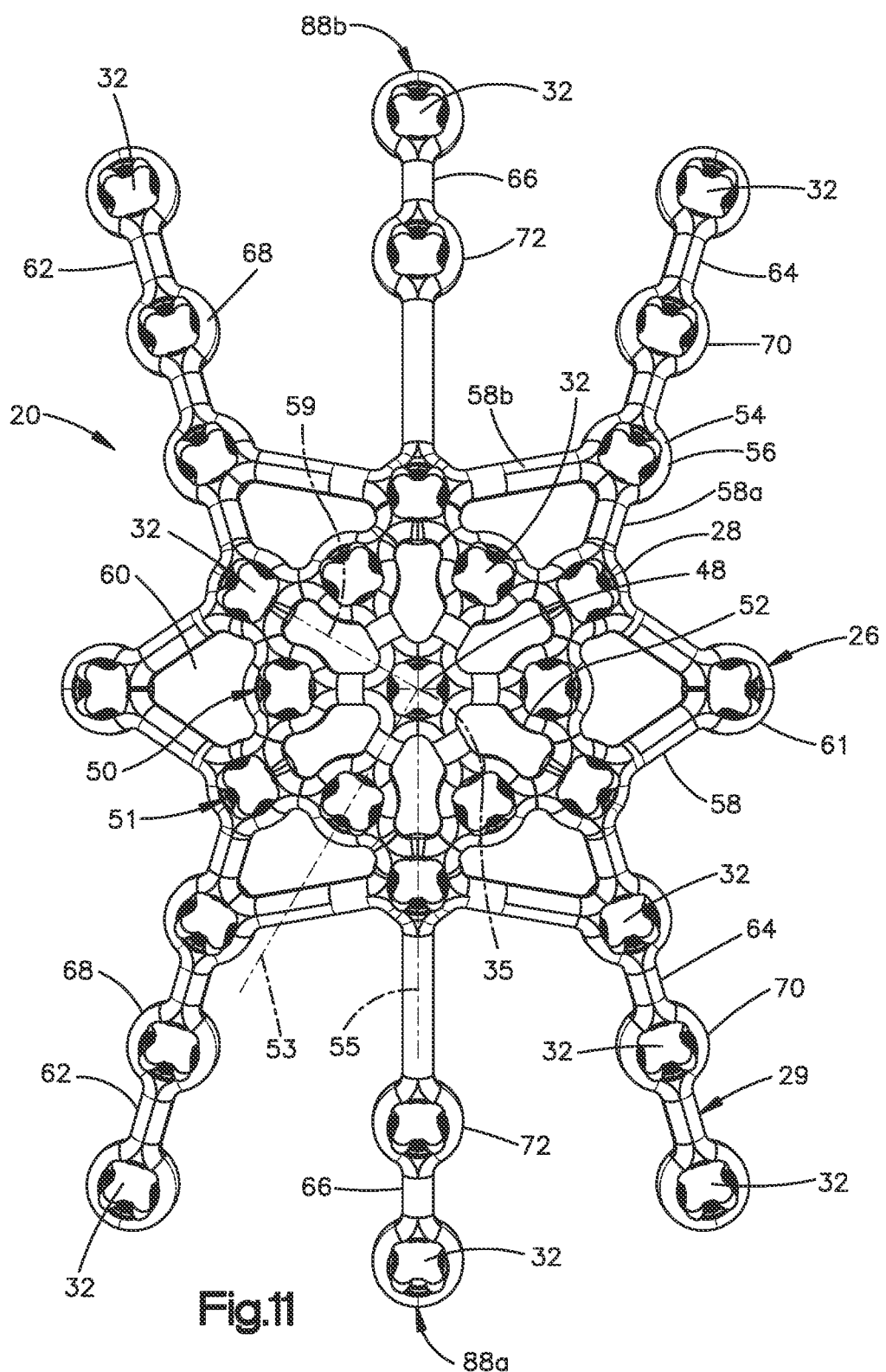
FIG. 11 is a perspective view of a bone plate similar to the bone plate illustrated in FIG. 6A, but shown having first and second groups of fixation legs.

As described above, the bone plate 20 can include a group of at least one fixation leg 29. However, as illustrated in FIG. 11, the bone plate 20 can include first and second groups 88a and 88b of at least one fixation leg. The first and second groups 88a and 88b can be positioned substantially opposite each other. Thus, the at least one leg 29 of one of the first and second groups 88a and 88b can extend inferiorly from the fixation body 26 in the manner described above, and the at least one leg 29 of one of the other of the first and second groups 88a and 88b can extend superiorly from the fixation body 26 in the manner described above. Alternatively, the at least one leg 29 of one of the first and second groups 88a and 88b can extend medially from the fixation body 26 in the manner described above, and the at least one leg 29 of the other of the first and second groups 88a and 88b can extend laterally from the fixation body 26 in the manner described above.

As illustrated in FIG. 11, the first and second groups 88a and 88b can be spaced at substantially 180 degrees from each other, such that the first and second groups 88a and 88b are opposite each other. It should be appreciated, of course, that the first and second groups 88a and 88b can be spaced from each other at any angle as desired. For instance, the first and second groups 88a and 88b can be spaced at substantially 90 degrees circumferentially from each other. Thus, the at least one leg 29 of one of the first and second groups 88a and 88b can extend inferiorly from the fixation body 26 in the manner described above, and the at least one leg 29 of the other of the first and second groups 88a and 88b can extend medially or laterally from the fixation body 26 in the manner described above. Alternatively, the at least one leg 29 of one of the first and second groups 88a and 88b can extend superiorly from the fixation body 26 in the manner described above, and the at least one leg 29 of the other of the first and second groups 88a and 88b can extend medially or laterally from the fixation body 26 in the manner described above. Alternatively still, the bone plate 20 can include three or more groups of at least one fixation leg 29. For instance, the bone plate 20 can include three groups of at least one fixation leg equidistantly spaced about the fixation body 26. Alternatively, the three groups can be spaced at different distances from each other. For instance, adjacent pars of the three groups can be spaced at substantially 90 degrees from each other, and one adjacent pair of the three groups can be spaced at substantially 180 degrees from each other. In another example, the bone plate can include four groups of at least one fixation leg 29 that are spaced equidistantly from each other. Thus, the at least one fixation leg 29 of a first group of the four groups can extend inferiorly from the fixation body 26 in the manner descried above, the at least one fixation leg of a second group of the four groups can extend superiorly from the fixation body 26 in the manner descried above, the at least one fixation leg of a third group of the four groups can extend medially from the fixation body 26 in the manner descried above, and the at least one fixation leg of a fourth group of the four groups can extend laterally from the fixation body 26 in the manner descried above.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

What is claimed:

1. A bone plate including:
   a plate body that defines a bone-facing body surface configured to face a bone and an outer body surface opposite the bone-facing body surface, wherein:
   the bone plate defines a first aperture that extends through the plate body from the outer body surface to the bone-facing body surface along a central first aperture axis,
   the plate body defines a first direction, a second direction perpendicular to the first direction, and a third direction opposite the second direction and perpendicular to the first direction, and
   the bone plate defines a plurality of fixation holes that extend through the plate body from the outer body surface to the bone-facing body surface along respective central axes and are each configured to receive a respective bone anchor, wherein the first aperture is disposed between first and second ones of the fixation holes with respect to the first direction, such that a first straight line that passes through the first aperture and is oriented along the first direction also passes through the first and second ones of the fixation holes, and
   the plurality of fixation holes further includes third and fourth ones of the plurality of fixation holes that are offset in their respective entireties from the first aperture in the second direction, such that 1) a second straight line that is oriented along the first direction and extends through the third one of the plurality of fixation holes also passes through the fourth one of the plurality of fixation holes, 2) no straight line that is oriented in the first direction that passes through the third and fourth ones of the plurality of fixation holes also passes through the first aperture, and 3) a central axis of the third one of the plurality of fixation holes is disposed between respective central axes of the first and second ones of the plurality of fixation holes with respect to the first direction;
   a first leg that extends from the plate body along the third direction at a location aligned with the first aperture along the third direction, wherein the first leg defines a respective first fixation hole that is configured to receive a first respective bone anchor; and a second leg that extends from the plate body and defines a respective second fixation hole that is configured to receive a second respective bone anchor, wherein the first and second legs are the only legs that extend from the plate body.

2. The bone plate of claim 1, wherein the first leg supports a first eyelet at an end of the first leg, the respective first fixation hole extends through the first eyelet, the second leg supports a second eyelet at an end of the second leg, and the respective second fixation hole extends through the second eyelet.

3. The bone plate of claim 2, wherein the first eyelet and the second eyelet are both offset from the bone plate body in the third direction.

4. The bone plate of claim 2, wherein the first and second legs have respective heights that are less than heights of the first and second eyelets, respectively, the heights measured along a direction perpendicular to each of the first, second, and third directions.

5. The bone plate of claim 1, wherein the plurality of fixation holes and the respective first and second fixation holes define variable angle threading.

6. The bone plate of claim 1, wherein the respective first fixation hole is the only hole that is supported by the first leg, and the respective second fixation hole is the only hole that is supported by the second leg.

7. The bone plate of claim 1, wherein the plurality of fixation holes comprises differently sized fixation holes that extend through the bone plate body.

8. The bone plate of claim 1, wherein each of the first and second legs is flexible.

9. The bone plate of claim 1, wherein the first aperture has a perimeter defined by a first end, a second end opposite the first end, and an inner edge that extends from the first end to the second end, wherein the inner edge tapers in width from a maximum width of the inner edge located adjacent the second end to a minimum width located adjacent the first end.

10. The bone plate of claim 9, wherein a length of the inner edge between the maximum width and the minimum width is substantially linear.

11. The bone plate of claim 10, wherein the first aperture defines a through-hole that extends through the bone plate.

12. The bone plate of claim 1, wherein a central axis of the fourth one of the plurality of fixation holes is disposed between the first and second ones of the plurality of fixation holes with respect to the first direction.

13. The bone plate of claim 1, wherein the second leg flares away from the first leg as the second leg extends from the plate body.

* * * * *